(12) United States Patent
Farrell

(10) Patent No.: US 7,404,403 B2
(45) Date of Patent: *Jul. 29, 2008

(54) ORAL APPLIANCE

(76) Inventor: Christopher John Farrell, 1st Floor, Helensvale Plaza, Sir John Overall Drive, Helensvale 4210, Queensland (AU)

( * ) Notice: Subject to any disclaimer, the term of this patent is extended or adjusted under 35 U.S.C. 154(b) by 689 days.

This patent is subject to a terminal disclaimer.

(21) Appl. No.: 10/639,149

(22) Filed: Aug. 11, 2003

(65) Prior Publication Data

US 2004/0103905 A1 Jun. 3, 2004

Related U.S. Application Data

(63) Continuation-in-part of application No. 10/232,240, filed on Aug. 30, 2002, now Pat. No. 6,637,436, and a continuation-in-part of application No. 10/070,349, filed as application No. PCT/AU99/00840 on Sep. 29, 1999, now Pat. No. 6,935,857.

(51) Int. Cl.
*A61C 5/14* (2006.01)
(52) U.S. Cl. .................. 128/859; 128/861; 128/862
(58) Field of Classification Search ............... 128/846, 128/848, 859–862; 602/902; 433/6
See application file for complete search history.

(56) References Cited

U.S. PATENT DOCUMENTS

| 4,955,393 | A | * | 9/1990 | Adell .................... 128/859 |
| 5,092,346 | A | | 3/1992 | Hays et al. |
| 5,190,051 | A | * | 3/1993 | Wilson .................... 600/590 |
| 5,259,762 | A | | 11/1993 | Farrell |
| 5,339,832 | A | * | 8/1994 | Kittelsen et al. ........... 128/862 |
| 5,406,963 | A | | 4/1995 | Adell |
| 5,566,684 | A | * | 10/1996 | Wagner .................... 128/861 |
| 5,624,257 | A | | 4/1997 | Farrell |
| 5,746,221 | A | * | 5/1998 | Jones et al. ............... 128/859 |
| 5,826,581 | A | | 10/1998 | Yoshida |
| 6,082,363 | A | * | 7/2000 | Washburn ................. 128/859 |
| 6,584,978 | B1 | | 7/2003 | Brett et al. |
| 2006/0219250 | A1 | * | 10/2006 | Farrell ..................... 128/859 |

FOREIGN PATENT DOCUMENTS

| CA | 2024799 | 7/1991 |
| EP | 801937 A | 10/1997 |
| FR | 2639531 A | 6/1990 |
| WO | WO 93/08761 | 5/1993 |
| WO | WO 95/23013 A1 | 8/1995 |
| WO | WO 00/35369 A1 | 6/2000 |

* cited by examiner

*Primary Examiner*—Michael Brown
(74) *Attorney, Agent, or Firm*—Caesar, Rivise, Bernstein, Cohen & Pokotilow, Ltd.

(57) ABSTRACT

A sports guard 1 for placing in a mouth of a user is disclosed. The guard 1 includes generally a base member 2 having a generally U-shaped form corresponding to the outline of a jaw of a user defining an upper channel 10 within which an upper row of teeth of a user can be received. The guard also discloses a teeth engaging element 3, associated with the channel 10 which is made of a material able to be user conformed or user moulded to the mouth of the user. The guard also includes shock absorption means associated with the base member 2 for absorbing impact shock. The shock absorption means comprises open channels in the base member 2 that function much like air springs. Further the base member advantageously comprises polyethylene mixed with up to 10% of EVA. The addition of EVA gives the guard more flexibility. The teeth engaging element is made of EVA.

13 Claims, 28 Drawing Sheets

ORAL APPLIANCE

RELATED APPLICATIONS

This application claims priority of Australian Provisional Application No. 200302996, filed Jun. 13, 2003. It is also a Continuation-in-Part of U.S. application Ser. No. 10/232,240, filed on Aug. 30, 2002, now U.S. Pat. No. 6,637,436 entitled "Oral Appliance Suitable for Use as Sports Guard." This application is a Continuation-in-Part of U.S. application Ser. No. 10/070,349, filed on Feb. 28, 2002, now U.S. Pat. No. 6,935,857 entitled "Oral Appliance Suitable for Use as Sports Guard", which in turn is a 371 of PCT/AU99/00840, filed Sep. 29, 1999, claiming priority from Australian Patent Application Nos. PP 7743 and PQ 1386, filed Dec. 16, 1998 and Jul. 2, 1999, respectively.

FIELD OF THE INVENTION

This invention relates to an oral or mouth appliance and to a method of making the appliance.

This invention relates particularly but not exclusively to an oral appliance that is a sports guard for protecting the teeth of a user in contact sports such as boxing, football, gridiron and rugby. It will therefore be convenient to hereinafter describe the invention with reference to this example application. It is to be clearly understood however that the invention is capable of broader application. For example the invention also extends to an appliance that is an orthodontic appliance.

BACKGROUND TO THE INVENTION

Customised sports mouthguards are known. Typically they are made by taking a mould or impression of a user's mouth and then moulding the guard individually from this impression to fit the specific and unique mouth of the user. While these customised guards obviously fit well in the user's mouth, it will be readily understood that this method of making sports guards is expensive as each guard is made to custom fit the user's mouth. Mass produced sports guards often do not produce a close fit and the protection that they provide is reduced as a result. This has limited their acceptance in the market place despite a clear need for an efficacious mass produced sports guard.

A further limitation of existing custom made and mass produced sports guards is that they are relatively soft and they offer only limited protection to the front teeth. If a blow strikes the front of the mouthguard, the guard tends to deform, so that the brunt of the blow is borne by the front teeth. This makes the front teeth vulnerable to being damaged or dislodged. It would be better if the force was transferred to all the teeth and particularly through to the back teeth that are particularly firmly anchored to the jaw.

Clearly it would be advantageous if a guard could be devised that had the strength and rigidity to transfer the force rearwardly so that the force is spread over all the teeth and particularly the back teeth. Clearly it would also be advantageous if a guard could be devised that had the fit of a custom made guard but that was mass produced and easy to fit in a domestic environment.

It would also be advantageous if a guard could be devised that was very efficacious at dissipating the energy of an impact. This would reduce the potential for injury or trauma to a user.

It is an object of the invention to provide a sports guard that ameliorates at least some of the shortcomings of the prior art described above.

SUMMARY OF THE INVENTION

According to one aspect of this invention there is provided an oral appliance for placing in the mouth of a user, comprising a base member having a generally U-shaped form corresponding to the outline of a jaw of a user, the base member defining at least one channel within which an upper or lower row of teeth of a user can be received, a teeth engaging element, associated with each channel, being made of a material able to be user conformed or user molded to suit the individual mouth of the user, and shock absorption means associated with the base member and/or the teeth engaging element for absorbing impact shock.

The appliance may be a sportsguard and the base member may be more rigid than the teeth engaging element.

Thus the upper and lower teeth engaging elements are capable of being molded to suit the teeth and jaws of a particular user by being heated above their softening point and then inserted into the mouth of the user.

The base member provides a degree of rigidity and impact resistance to the mouthguard. This assists in transferring the force of the blow across the full surface area of the guard. The shock absorbers enable at least part of the force of an impact to be substantially absorbed or dissipated by the mouthguard instead of being transmitted to the jaw, specifically the temporo-mandibular joints and on into the skull.

While EVA is preferred for the teeth engaging elements, any thermoplastic having a suitable softening temperature may be used. Preferably the element is malleable at a temperature below 100° C., e.g. so that it can be softened by immersion in boiling water.

The layer of thermoplastic material, e.g. EVA, may have a thickness of 1 mm-4 mm, preferably 1 mm-3 mm, e.g. about 2 mm. EVA has a suitable level of pliability and formability when heated to its softening temperature.

In order to provide increased stability the continuous layer of thermoplastics material preferably substantially covers the complete surface area of the base member.

Thus the continuous layer also covers a region of the base member intermediate the upper and lower channels, e.g. the outer walls of the flanges, as well as the channels. The layer encases the base member to firmly and securely mount teeth engaging elements on the base member without delamination. This helps to overcome the problem of getting EVA to bond to the base member.

It is to be understood however that this arrangement is not essential and that the layer may be continuous without covering the entire surface area of the base member.

In this specification, the term "engaging" shall bear a broad meaning and shall not be interpreted to mean "retaining" or "latching engagement".

The shock absorption means preferably comprises one or more pre-designated compressible areas associated with the base member. Conceivably the shock absorption means could also comprise compressible areas defined in the teeth engaging elements.

In a preferred embodiment the shock absorption means comprise one or more spacings defined in the base member. The shock absorbers may take the form of one or more open or closed air channels defined in the base member. These air channels may extend from an outer face of the base member through the base member to an inner face of the base member.

Accordingly the guard comprises not only a material based impact absorption but also an additional 'spring air' system which provides shock absorption very much like the leaf springs in a motor vehicle. The provision of the spacings provides a better absorption of impact than a completely solid material. As such a comfortable absorption of shock is effected and the mouthguard is loaded in a progressive manner. Increasing impact force does not lead to complete depression or collapse since the force required to compress the shock absorbers exponentially increases with deflection similar to a rising rate suspension. This feature absorbs a considerable amount of the energy transferred by a large impact.

The open channels may have dimensions of height lying in the range of 0.5-10 mm, preferably 1.5-5 mm. The open channels may have dimensions of length lying in the range of 0.5-30 mm.

Preferably the shock absorption means takes the form of side open channels arranged in or near terminal ends of the generally U-shaped form of the base member and/or at least one frontal open channel arranged in a front section of the base member.

The frontal open channel may have a length lying in the range 2-10 mm, preferably 4-8 mm.

Preferably the side open channels are arranged in or near the terminal ends of the generally U-shaped form of the base member and have a length of between 10-20 mm.

The layer of thermoplastic material may define one or more openings which correspond with at least one or more of the open channels defined in the base member.

Optionally the layer of thermoplastic material can cover the openings of the open channels to define a closed space. This provides extra air pressure during deflection, since the EVA outer covering, if closed over the "air springs" increases air pressure during deflection.

The base member may be made of a plastics material, preferably being non-thermoplastic below about 100° C. and having a degree of flexibility. Preferably the base member is substantially rigid at temperatures of 90° C.-95° C. and is not user conformable or moldable in boiling water.

Preferably the base member comprises polyethylene, polyurethane, polypropylene and santoprine. Most preferably the base member comprises polyethylene, eg HDPE.

The base member may include 10% or less of a thermoplastic material in combination with the non thermoplastics material. Preferably the non thermoplastics material is polyethylene and the thermoplastic material is EVA. The EVA may be present in the range of 4-8% by weight of the base member, more preferably about 5%.

Thus the member may include a material having greater flexibility than polyethylene. The addition of EVA to the material comprising the base member improves the flexibility thereof. It may also assist in improving the adhesion of the base member to the teeth engaging element.

In one embodiment the base member has inner and outer flanges interconnected by a web which collectively define upper and lower channels within which the upper and lower rows of teeth of the user are receivable, and an upper teeth engaging element is mounted over the base member in the upper channel and a lower teeth engaging element is mounted over the base member in the lower channel.

In another embodiment the base member has inner and outer flanges interconnected by a web which collectively define an upper channel within which the upper teeth are received in use and a teeth engaging element is mounted over the base member within the upper channel. This guard is only mounted over the upper teeth. These upper arch sports guards are the type most commonly used for sports applications.

The base member may have a degree of flexibility to adapt to the arch of size of a user. Specifically this may comprise a cut-out or recess in the outer flange that permits the spacing of opposing sides of the base member to be adjusted.

A tongue tag can be formed on the inner flange of the base member, the tongue tag being substantially centrally positioned for correctly positioning the tongue of a user during use.

Furthermore the base member may be equipped with breathing apertures defined therein for facilitating breathing by a user when wearing the appliance.

The appliance may further include locating means for correctly locating and positioning the jaws in the teeth engaging element during fitting of the oral appliance. The locating means may comprise a brace arranged externally on the layer of thermoplastic material. The brace may be made of rubber.

According to another aspect of this invention there is provided an oral appliance for placing in a mouth of a user, the appliance including:

a base member having a generally U-shaped form corresponding to the outline of a jaw of a user, the base member defining at least one channel within which an upper or lower row of teeth of a user can be received, and wherein the base member is made of polyethylene with less than 10% by weight of a thermoplastics material, a teeth engaging element mounted over the base member in each channel made of a thermoplastics material that is able to be user conformed or user moulded to suit the individual mouth of the user.

According to yet another aspect of this invention there is provided a method of manufacturing an oral appliance as described above, comprising the steps of molding a base member from rigid material in a first molding step in a first mould, arranging one or more shock absorbing spacings in the base member and removing the base member from the first mould and placing it in a second mould having a larger mould cavity and molding a continuous layer of thermoplastic material onto the base member to form upper and lower teeth engaging elements capable of being customised to suit the mouth of a user, the layer encasing the member to thereby firmly and securely mount the layer of thermoplastic material on the base member.

Preferably the layer of thermoplastic material is injection molded from EVA while it is locked in position in the second mould.

Thus, the oral appliance may be formed in a two step injection molding process. More specifically, the base member may be injection molded in a first die or mould and then when it has been formed it is removed from the first die and locked into a second die or mould where the layer encasing the member is injection molded. Thus the teeth engaging elements surround or enclose the base member to effect attachment to the base member.

Alternately a co-injection molding process can be used where the base member and the layer of material is formed in the same mould. The second or subsequent injections follow a first injection and cover the entire base member with the layer of EVA. This process does not require removal of the base member to another die.

DETAILED DESCRIPTION OF THE INVENTION

An oral appliance in accordance with this invention may manifest itself in a variety of forms. It will be convenient to hereinafter provide a detailed description of several embodiments of the invention with reference to the accompanying drawings. The purpose of providing this detailed description is to instruct persons having an interest in the subject matter of the invention how to put the invention into practice. It is to be clearly understood however that the specific nature of this detailed description does not supersede the generality of the preceding statements. In the drawings.

Figure 1:
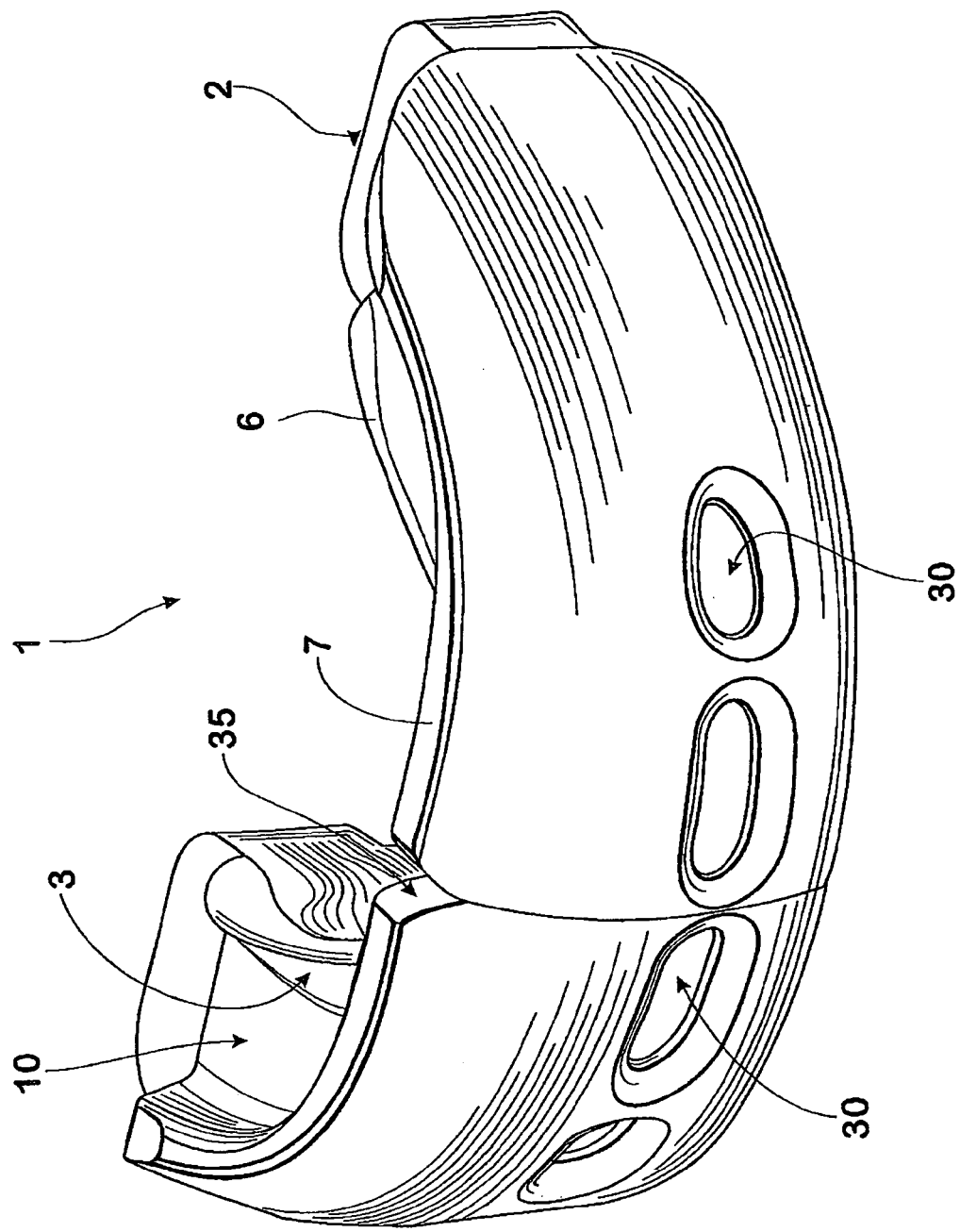
FIG. 1 is a front three dimensional view of an oral appliance in accordance with one embodiment of the invention.
Figure 2:
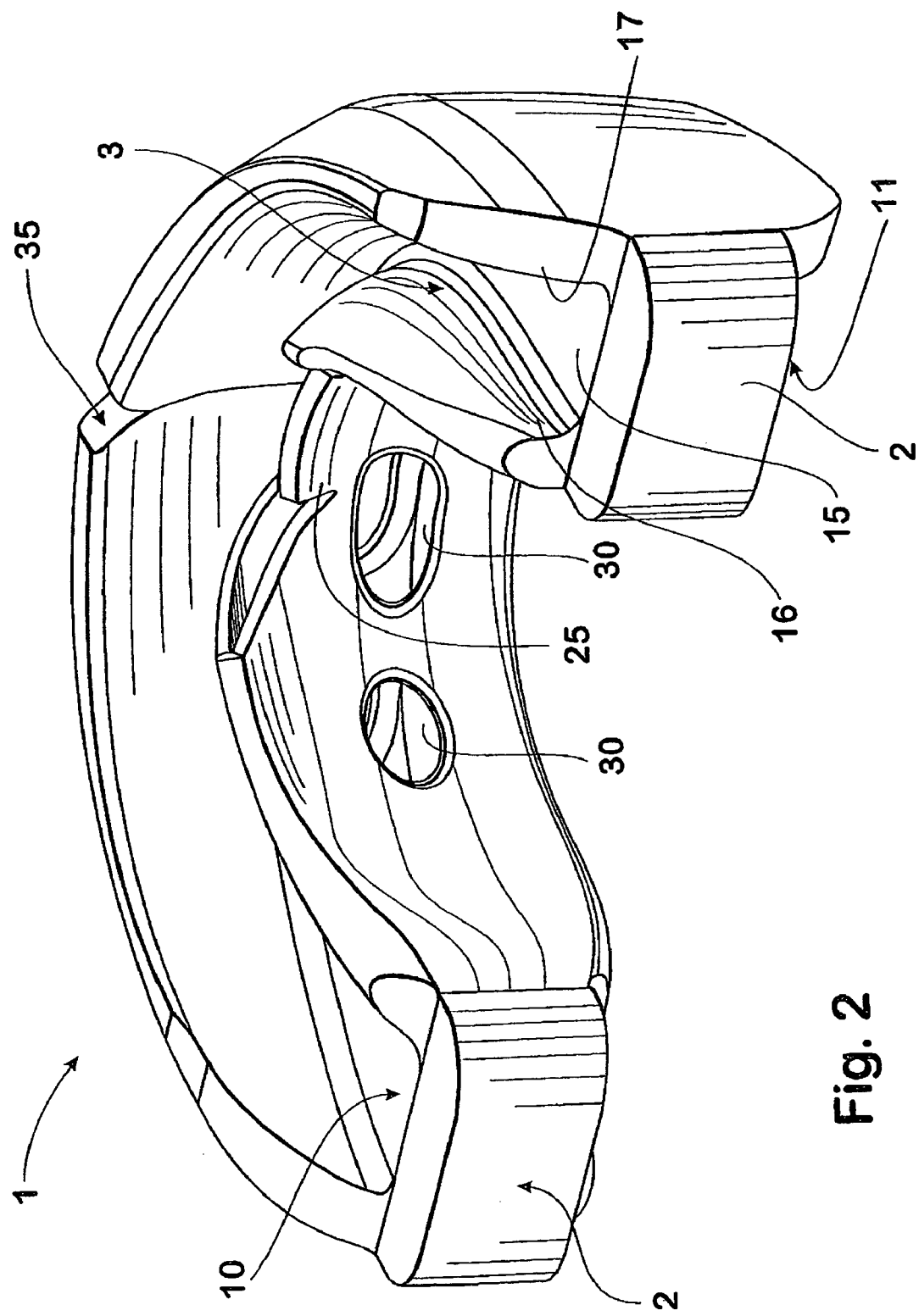
FIG. 2 is a rear three dimensional view of the oral appliance of FIG. 1.
Figure 3:
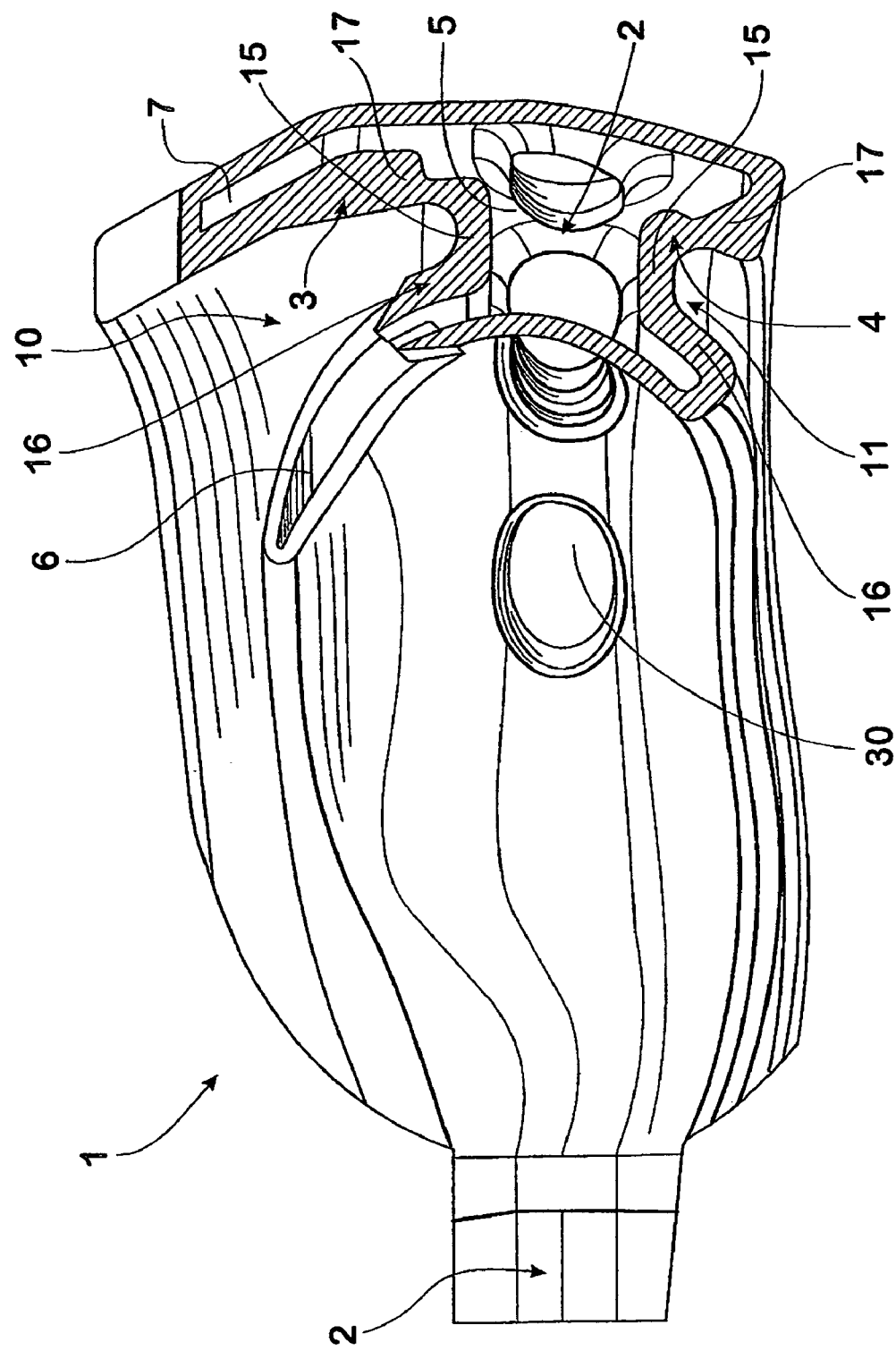
FIG. 3 is a part sectional side view of the appliance of FIG. 1.
Figure 4:
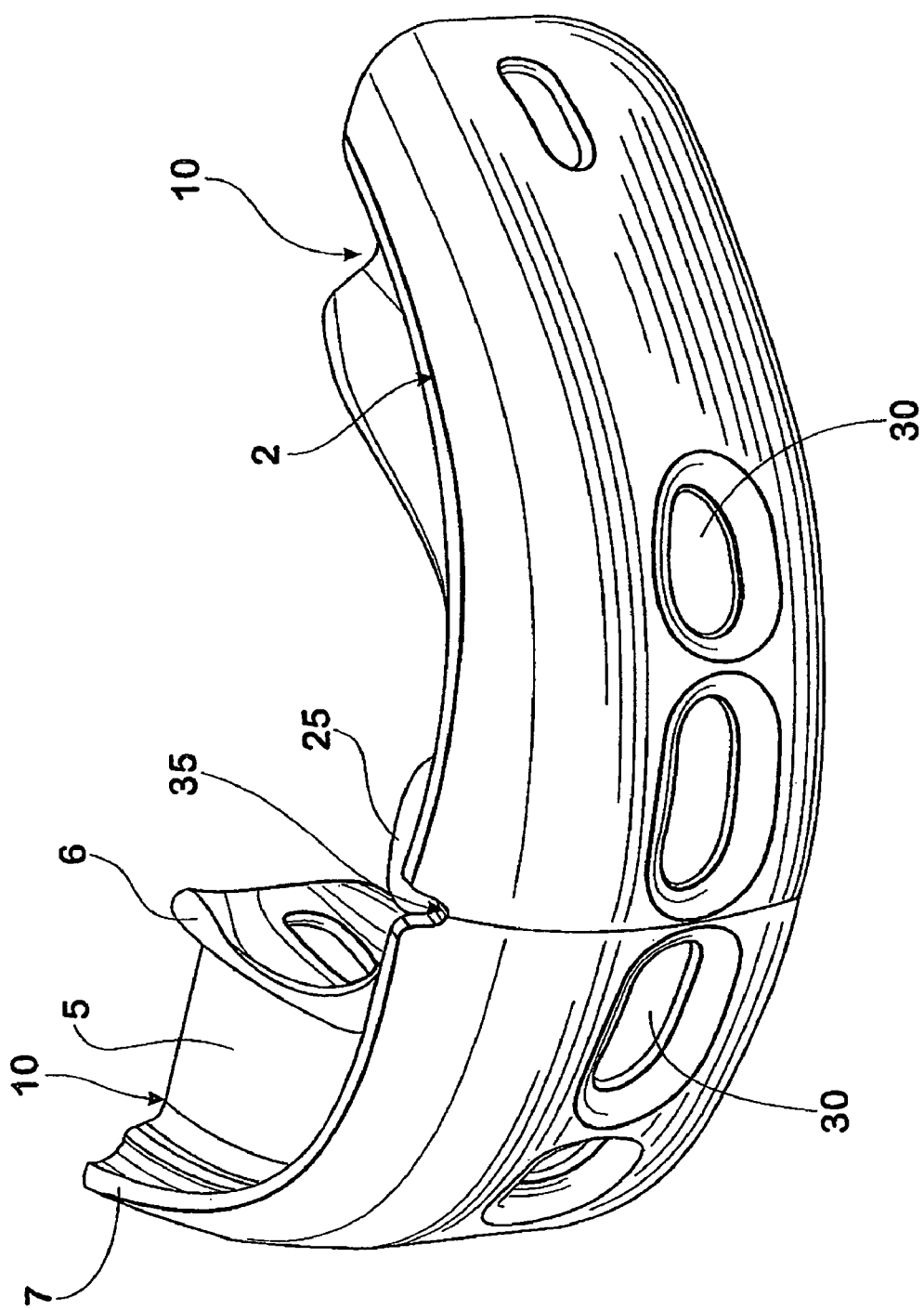
FIG. 4 is a front three dimensional view of the base member of the appliance of FIG. 1.
Figure 5:
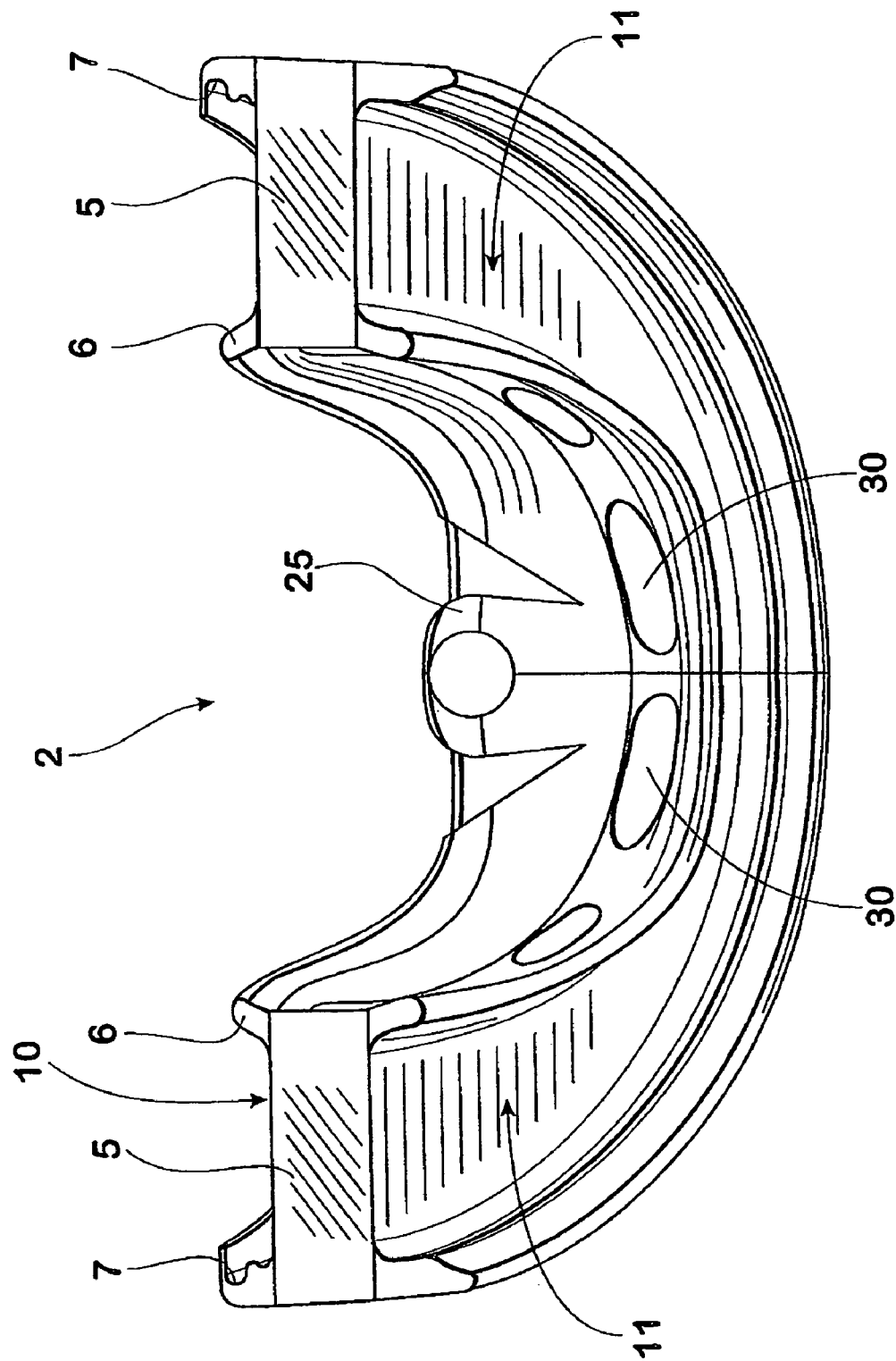
FIG. 5 is a rear three dimensional view of the base member of FIG. 4.

In FIGS. 1 to 5 reference numeral 1 refers generally to an appliance which may be a sports mouthguard in accordance with the invention.

The guard 1 comprises broadly a base member 2 having teeth engaging elements 3, 4 mounted on upper and lower surfaces of the member 2. This embodiment is thus a double arch appliance. A single arch guard that fits over the upper teeth will be described below with reference to other drawings.

The base member 2 has a broadly U-shaped configuration to complement the U-shape of the arch of a user. The base member 2 has a central web 5 and inner and outer flanges 6 and 7 projecting upwardly and downwardly from both the inner and outer edges of the web 5. The web 5 and the flanges 6 and 7 collectively define upper and lower channels 10 and 11 within which respectively the upper and lower teeth engaging elements 3 and 4 are positioned.

The base member 2 is made of a substantially rigid plastics material that is polyethylene which has been found to be the most suitable material. This has a high level of rigidity, hardness and durability while still permitting some limited flexing, ie to accommodate the different width of arches for different users. The polyethylene may be high density polyethylene (HDPE). A suitable high density polyethylene can be obtained from plastics suppliers such as Exxon Mobil Chemical Company. The material is generally supplied as a resin. The softening point of the resin is above 212 degrees Fahrenheit.

The teeth engaging elements 3, 4 are formed by a layer of thermoplastics material that is EVA (ethyl vinyl acetate) that encloses and encapsulates the base member 2. The layer has a thickness of 1 mm to 3 mm, typically about 2 mm. EVA has the property that it softens when it is heated to 90° C. to 95° C. This enables it to be shaped to conform to the arch and teeth of a user as will be described in more detail below.

In the illustrated embodiment the layer of EVA extends fully across the surface area of the base member and encases the base member continuously without any interruption, ie without any gaps or spaces.

The EVA appears to have some positive attachment to the polyethylene of the base member. Further the attachment of the layer of EVA to the base member is enhanced by the fact that it encases the base member continuously and extends across the full surface area of the base member. This helps to resist delamination of the two materials during of the appliance.

Each of the tooth engaging elements 3, 4 also has a broadly U-shaped configuration when viewed in plan view. This complements the general shape of the base member 2. Each element 3, 4 also has a broadly U-shaped cross-sectional configuration with a bottom wall 15 and two side walls 16 and 17. The shape and width of the channels defined in the base member 2 and elements 3, 4 have been specifically designed so as to enable the appliance to be capable of being fitted to a large number of patients.

In addition the appliance also includes a notch or cut-out 35 in the upper surface of the outer flange 7. The notch 35 has the important function of permitting inward or outward adjustment of the arms of the U-shaped member without causing distortion of the appliance 10. This enables a single appliance to fit patients with different arch sizes.

The guard has a tongue tag 25 for positioning the tongue of a user in a central position during use. The guard also has a number of holes 30 defined therein in the central region thereof that permit mouth breathing by a user. This is often required when playing sports.

A further feature of the guard is that the web of the member thickens from the front of the member to a point towards the rear of the base member just prior to the rear of the member. After this point the member starts thinning down again. This tends to fill in the space between the teeth of the upper and lower jaw. This in some respects resembles an aerofoil and thickens the member. This feature is described in detail in the applicant's earlier U.S. Pat. Nos. 5,259,762 and 5,624,257, the contents of which are incorporated directly herein by cross reference.

The guard is injected moulded in a two-stage injection moulding process. The base member is injection moulded in a first die from polyethylene. The base member is then removed from the first die and locked into a second die in which the EVA layer is injection moulded onto the base member. The base member is held in position by locking elements which are pins. It is particularly important that the base member does not move or flex when the layer of EVA is injection moulded onto it. The base member described above has been found to fully satisfy these requirements.

In earlier versions of these types of products the Applicant produced the base member from high density polyethylene without any other components mixed in with the plastics material. However Applicant has now produced a base member containing 93-97% by weight of polyethylene and 3-7% by weight of EVA. The EVA is blended in with the polyethylene at an early stage when the plastics are still being mixed. Applicant has found that the EVA makes the base member more flexible while still enabling it to perform its function.

Applicant has experimented with varying levels of EVA and has found a base member with up to 10% by weight of EVA produces reasonable results. Applicant currently prefers some EVA in his base members and feels that they offer better performance than the base members made solely of polyethylene. If more than 10% of EVA is contained in the base member it becomes too soft and flexible.

In use, the sports guard may easily be fitted in a domestic environment. This is done by immersing the guard in boiling water which causes the EVA to soften. Typically, this only takes a few minutes. The base member remains rigid at this temperature. Thereafter the guard is placed in the user's mouth where it moulds and conforms to the arch and teeth of the user's mouth. As it cools to body temperature in the mouth of the user it hardens in the shape that it is forced into and is therefore customised to snugly fit in the mouth of a user.

Applicant has found that polyethylene and EVA are compatible with each other and do not delaminate. Further when the appliance is subjected to flexing in use the polyethylene and EVA are able to flex together and resist delamination. Without being bound by theory Applicant believes that the levels of thermal expansion of the materials are compatible with each other. Also the ability of the materials to flex or stretch at their interfacing surfaces is comparable.

The layer of EVA is relatively thin so the guard is not excessively bulky in a user's mouth. This is an important feature that enables users to talk while they are wearing the guard. Talking is an important part of playing some contact sports.

Figure 6:
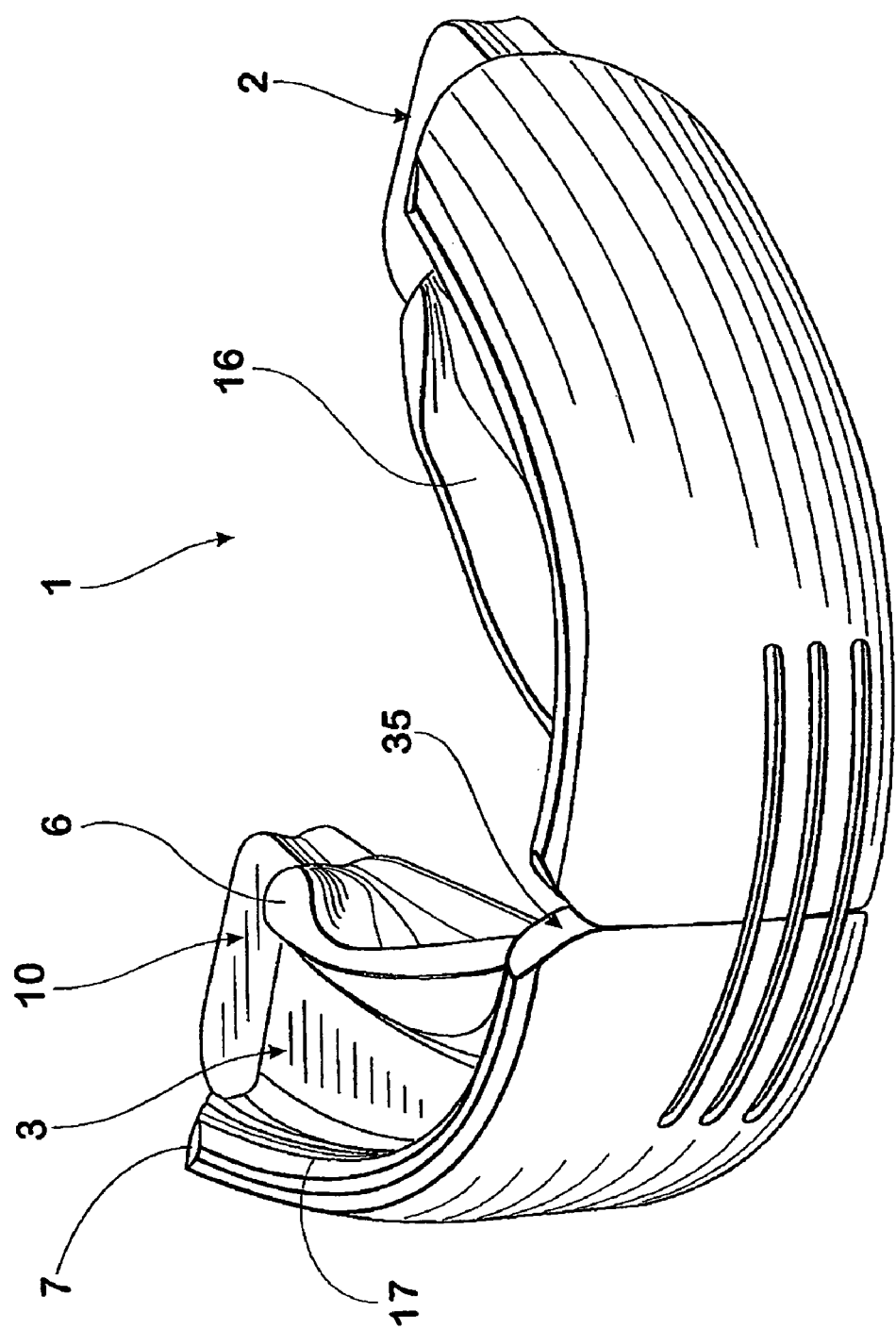
FIG. 6 is a front three dimensional view of an appliance in accordance with a second embodiment of the invention.
Figure 7:
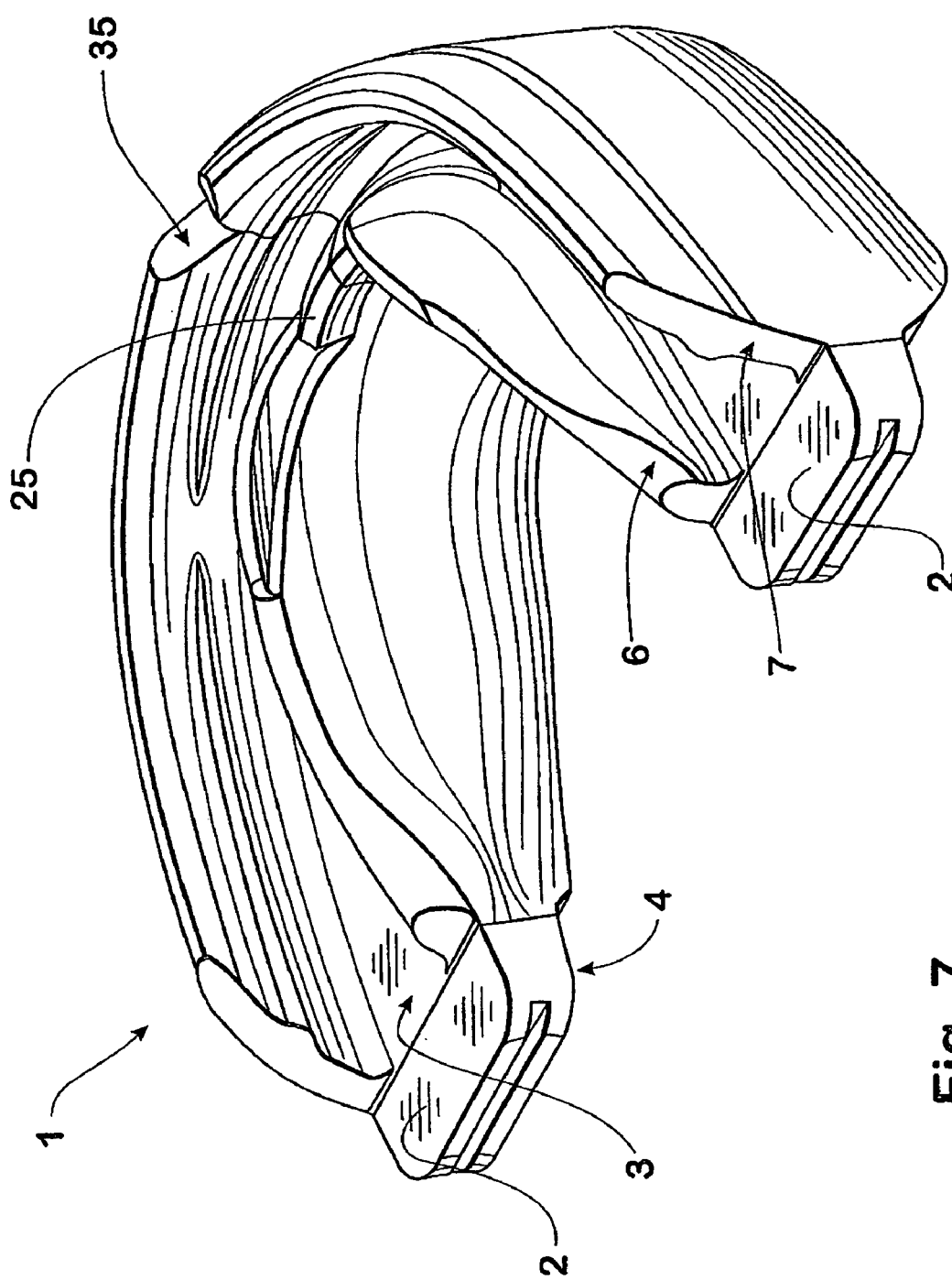
FIG. 7 is a rear three dimensional view of the appliance of FIG. 6.
Figure 8:
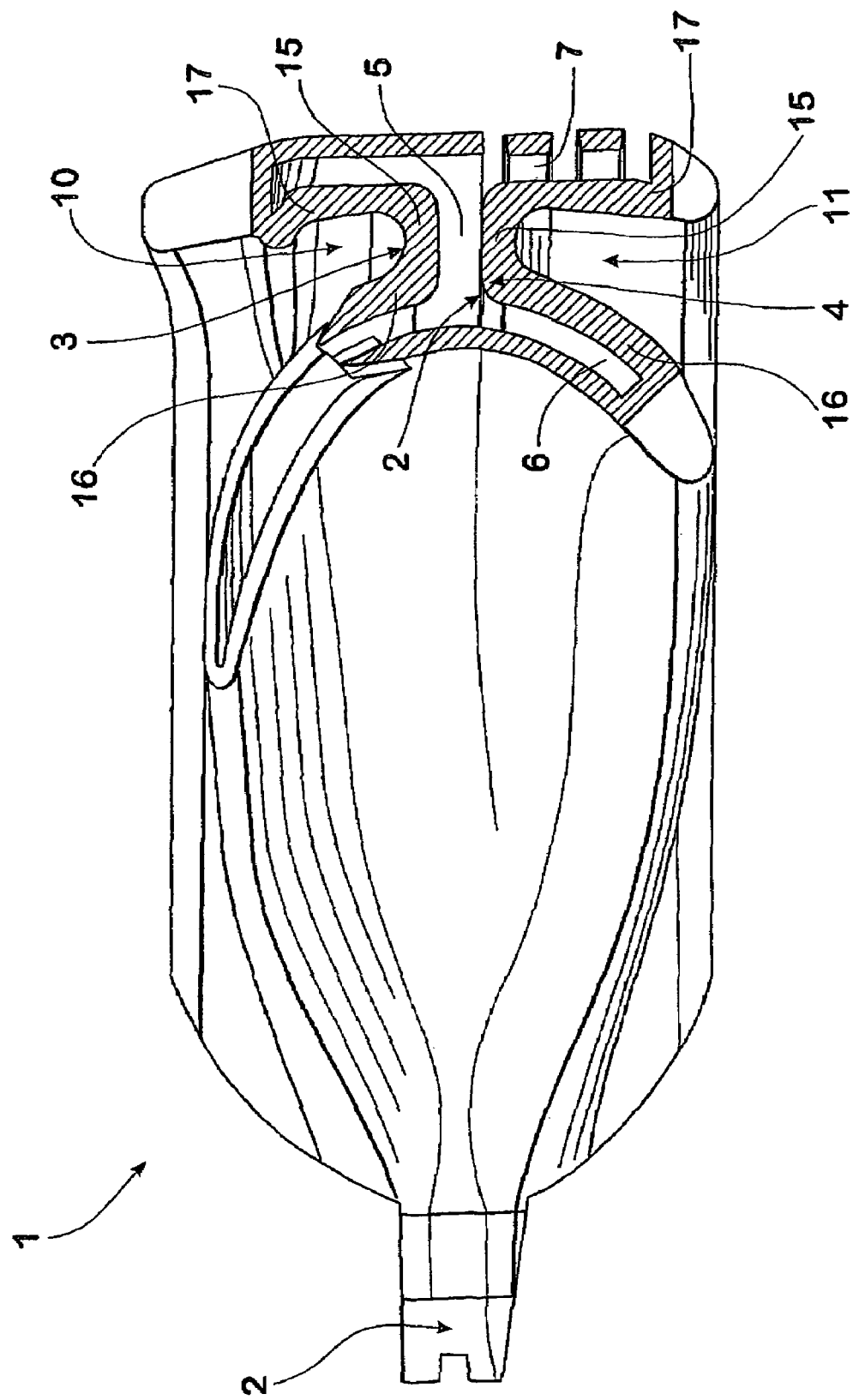
FIG. 8 is a part sectional side view of the appliance of FIG. 6.
Figure 9:
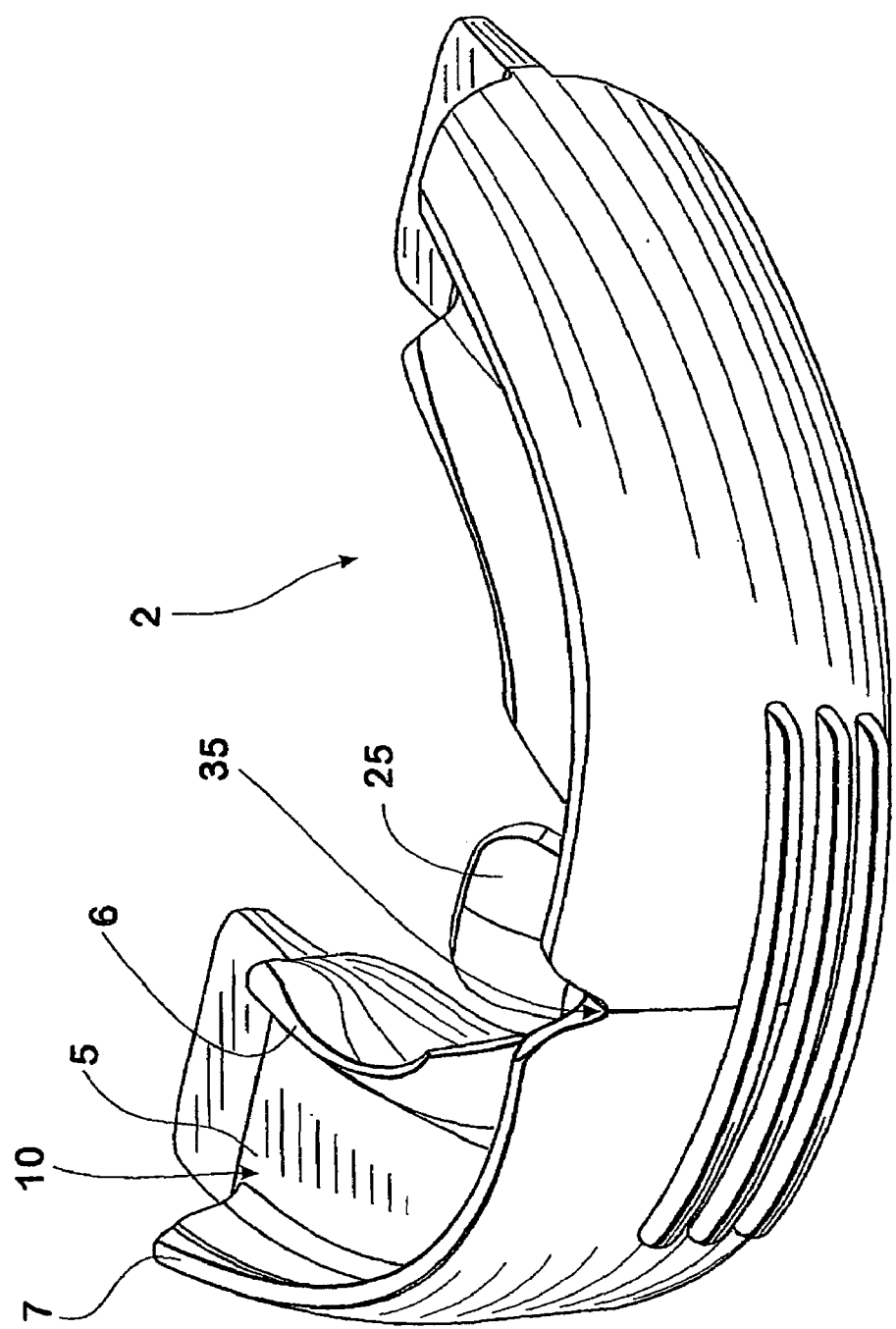
FIG. 9 is a front three dimensional view of the base member of the appliance of FIG. 6.
Figure 10:
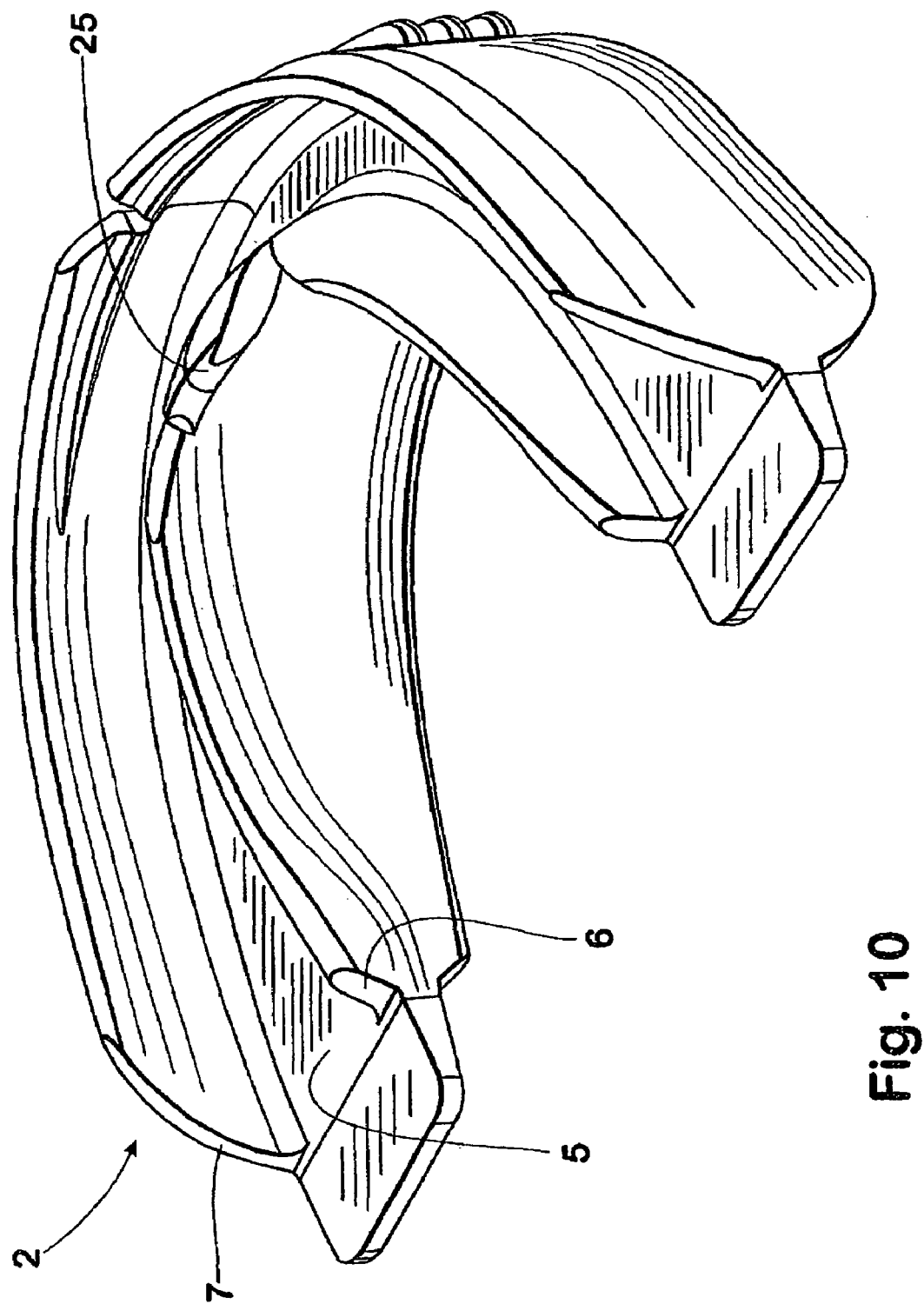
FIG. 10 is a rear three dimensional view of the base member of FIG. 9.
Figure 11:
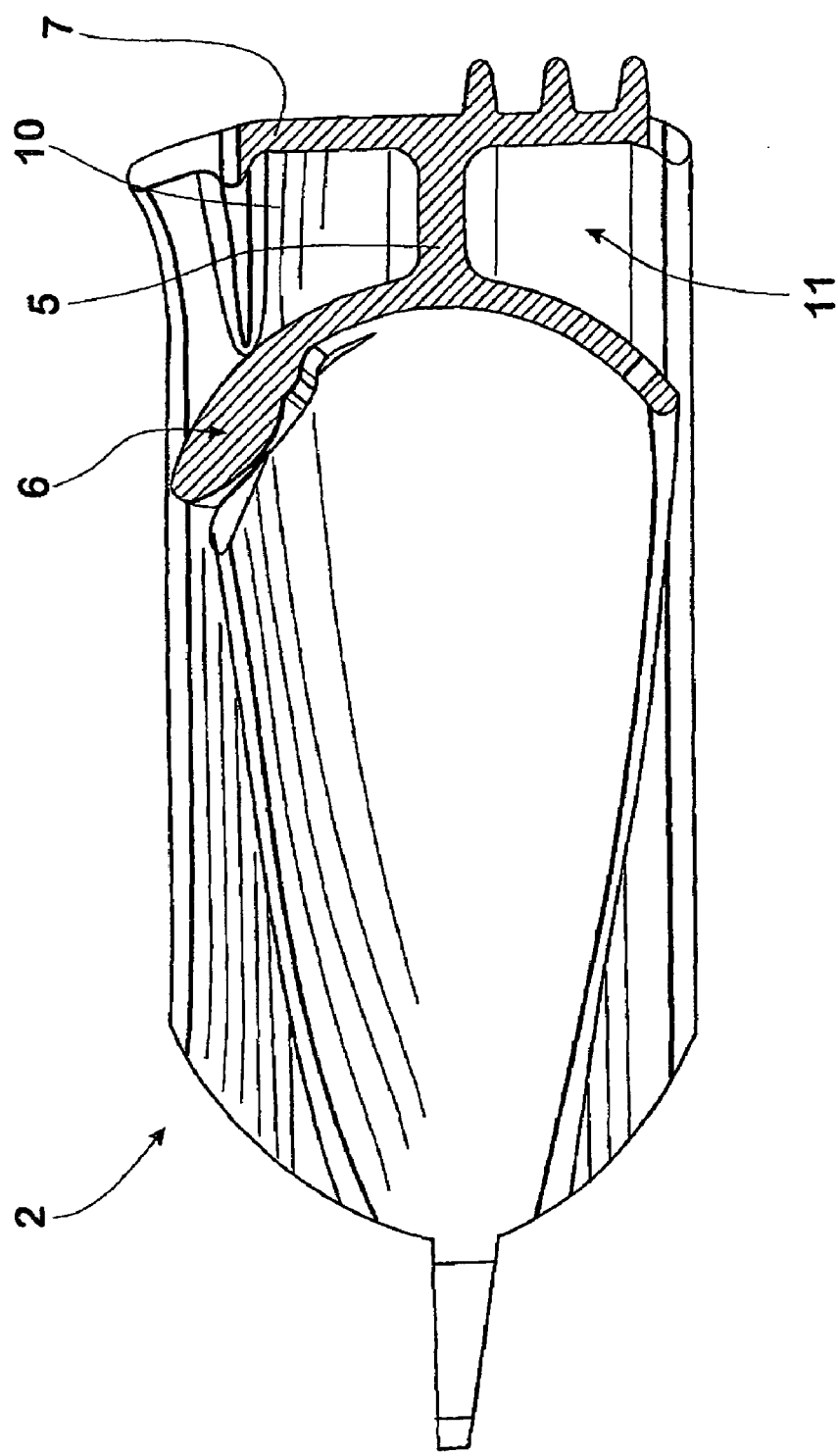
FIG. 11 is a sectional side view of the base member of FIG. 9.

In a second embodiment of the invention illustrated in FIGS. 5 to 11, the appliance is used for orthodontic treatment. The orthodontic appliance is the same as that illustrated in FIGS. 1 to 5 with the exception that it does not have breathing holes, eg for mouth breathing, and the base element 2 is thinner, eg having an approximate thickness of 2 mm to 4 mm, because it does not have the same requirements of mechanical strength as the sports guard. The orthodontic appliance is used for myofunctional training and tooth alignment. Myofunctional training is a clinical procedure which is designed to correct bad oral habits, eg tongue thrusting, mouth breathing, incorrect swallowing and the like.

In use the appliance is initially fitted by a dentist or orthodontist in a dental surgery. The shape of the elements 3, 4 prior to use corresponds broadly to an ideal positioning or "bite" of a patient's teeth. To enable the elements 3, 4 to be tailored to a patient's specific teeth, the elements 3, 4 are dipped into boiling water to soften the elements and then inserted into a patient's mouth to mould them to the specific contours of a patient's mouth.

The EVA material from which the elements 3, 4 are formed has a memory so that it reverts to its original shape when reheated. It reverts partly to its original shape when heated to 60° C. to 65° C. and fully to its original shape when heated above 90°C.

The memory properties of the EVA enable the elements 3, 4 to be used to progressively correct misalignment of a patient's teeth. For example at spaced time intervals, the dentist will typically place the appliance into water at a temperature of 60° C. to 65° C. which causes the elements 3, 4 to partly revert to their original shape. The slightly altered shape brought about by this remoulding causes the appliance to apply pressure to the teeth of a user to correct misalignment. This can be done several times until the patient's teeth take up the correct position or the ideal "bite" position.

When the teeth are in the correct position the appliance can be placed into water at 90° C. to 95° C. which causes it to revert to its original position. The appliance can then be used as a retaining device for retaining the teeth in the correct position and also for carrying out myofunctional training.

In the embodiments illustrated in FIGS. 1-11, 'air spring' shock absorbers are not shown.

Figure 12:
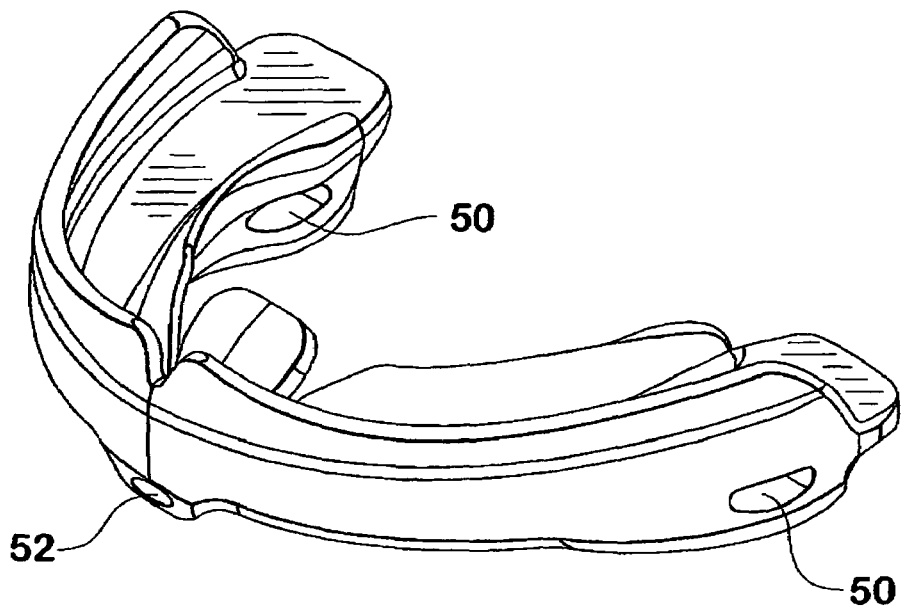
FIG. 12 is a perspective view of a base member for a mouthguard according to the present invention provided with a shock absorption system.
Figure 13:
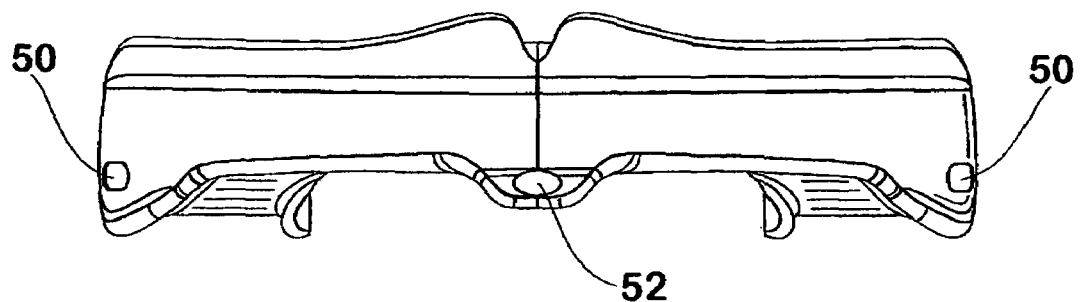
FIG. 13 is a rear view of the guard of FIG. 12.
Figure 14:
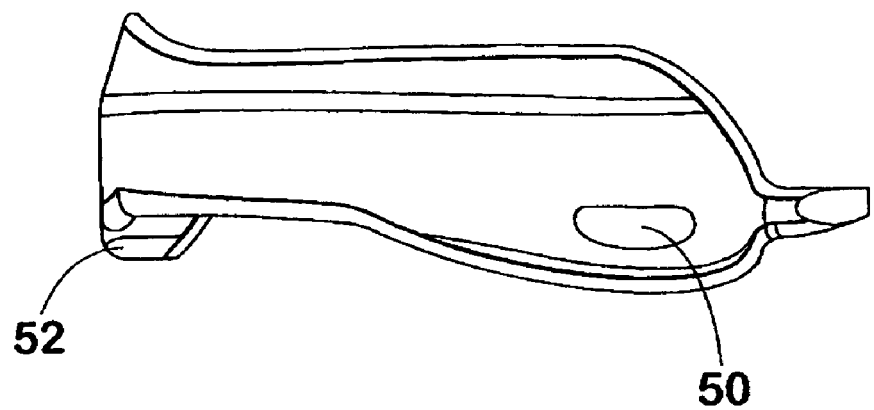
FIG. 14 is a side elevation of the guard shown in FIG. 12 and FIG. 13.
Figure 15:
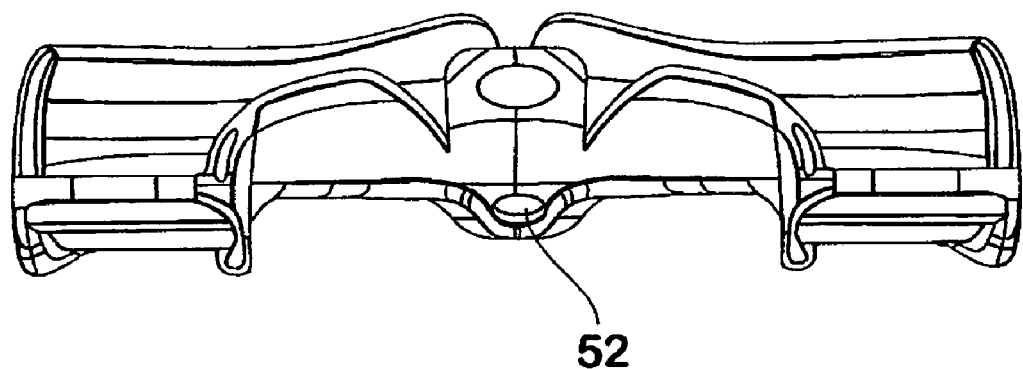
FIG. 15 is a rear view of another embodiment of a base member according to the present invention for a mouthguard having 'air spring' shock absorbers.
Figure 16:
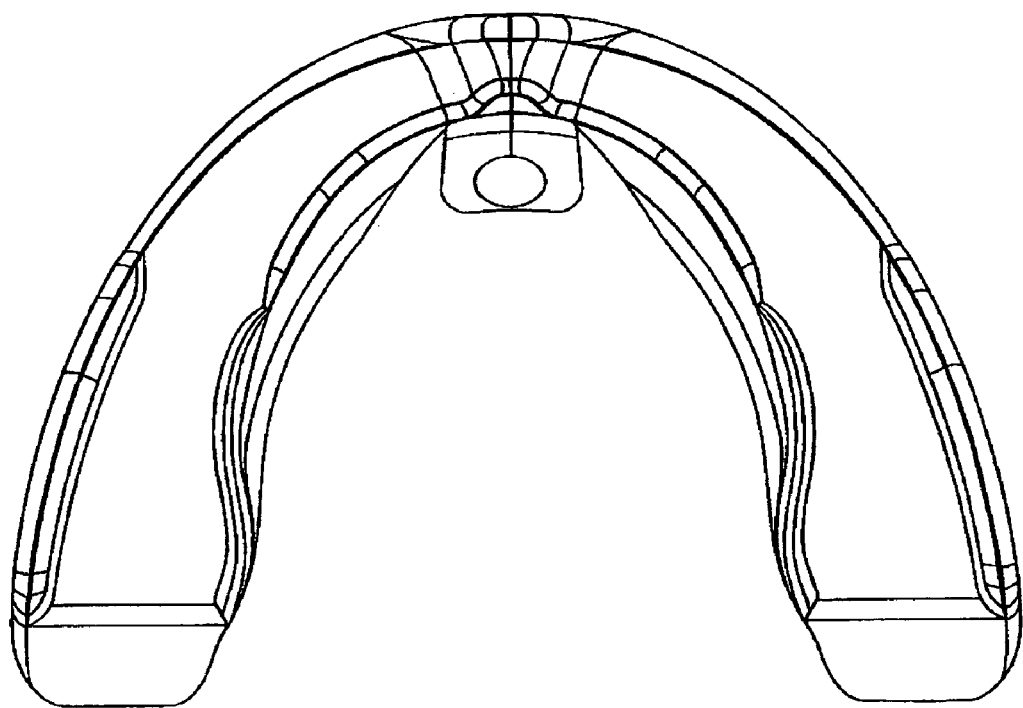
FIG. 16 is a top plan view of the guard shown in FIG. 15.
Figure 17:
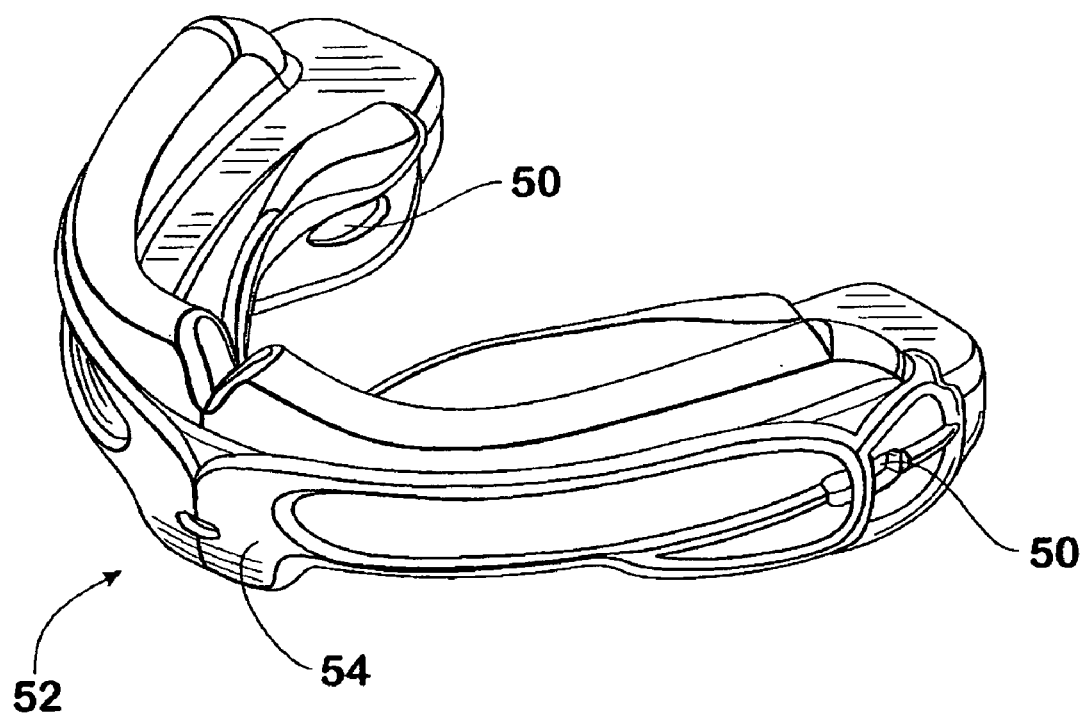
FIG. 17 is a three dimensional view of yet another embodiment of a guard illustrating openings in the thermoplastic layer which correspond with the 'air spring' shock absorber openings in the base member and also showing a brace element fitted around the front of the thermoplastic layer.
Figure 18:
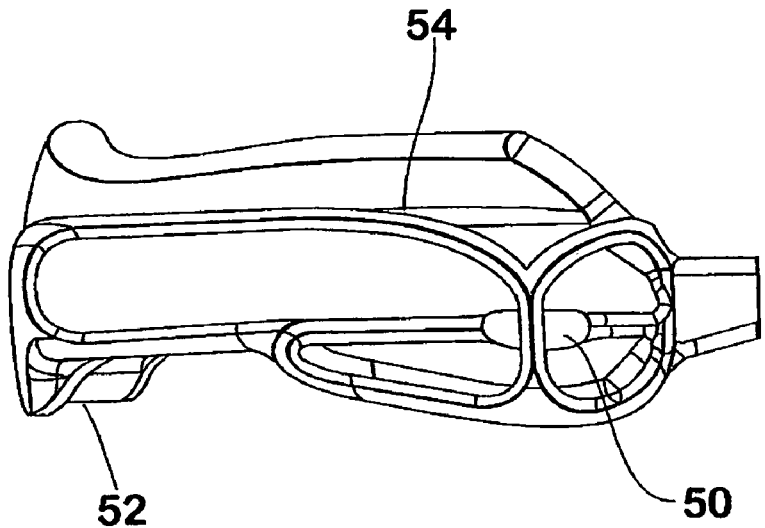
FIG. 18 is a side view of the guard shown in FIG. 17.
Figure 19:
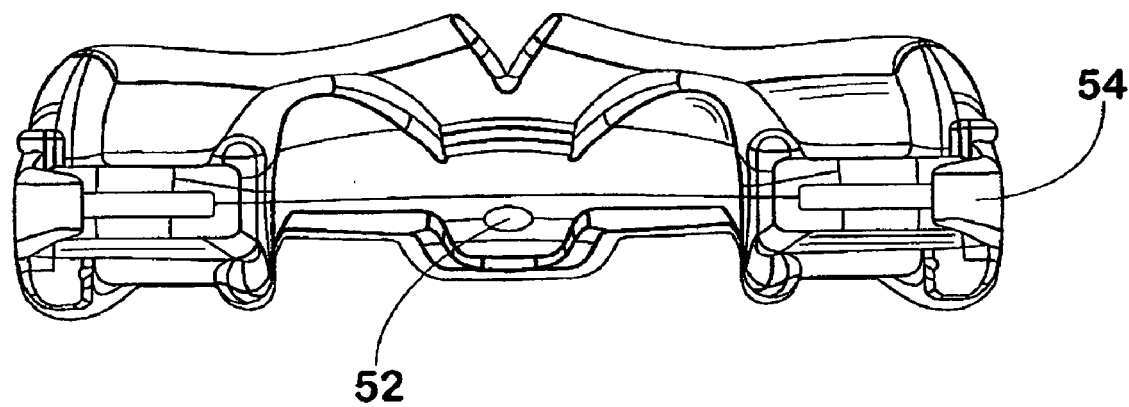
FIG. 19 is a rear view of the guard shown in FIG. 17 and FIG. 18.
Figure 20:
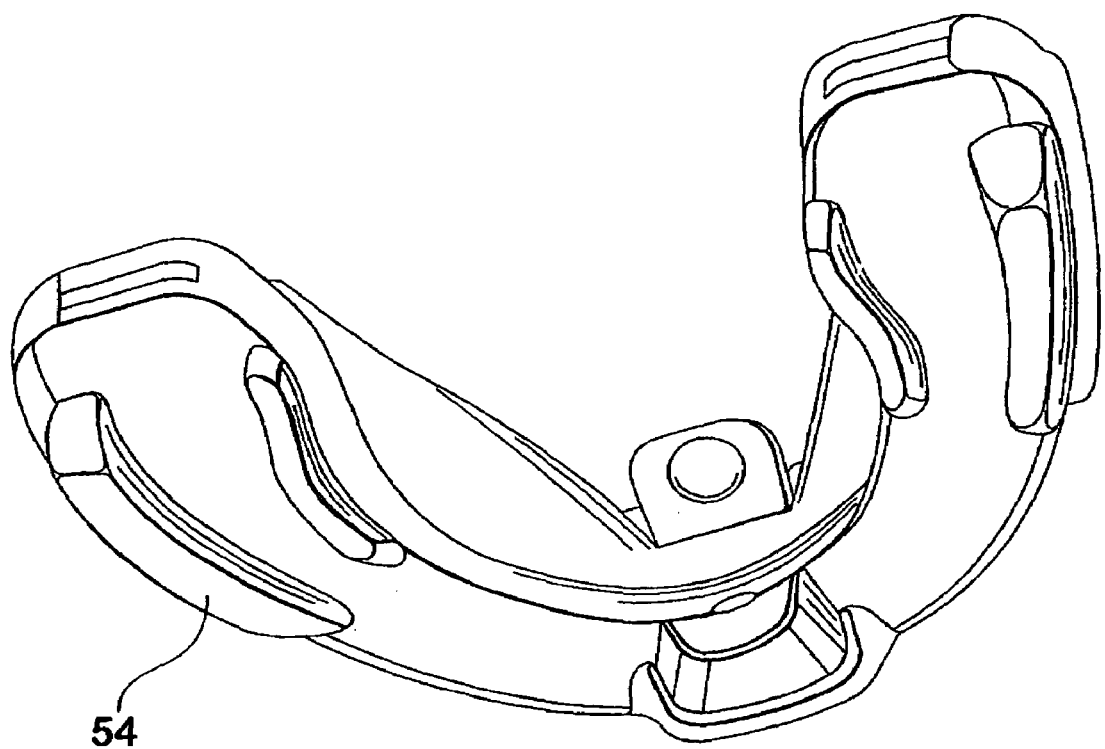
FIG. 20 is a rear three dimensional view of the embodiment shown in FIGS. 17-19.
Figure 21:
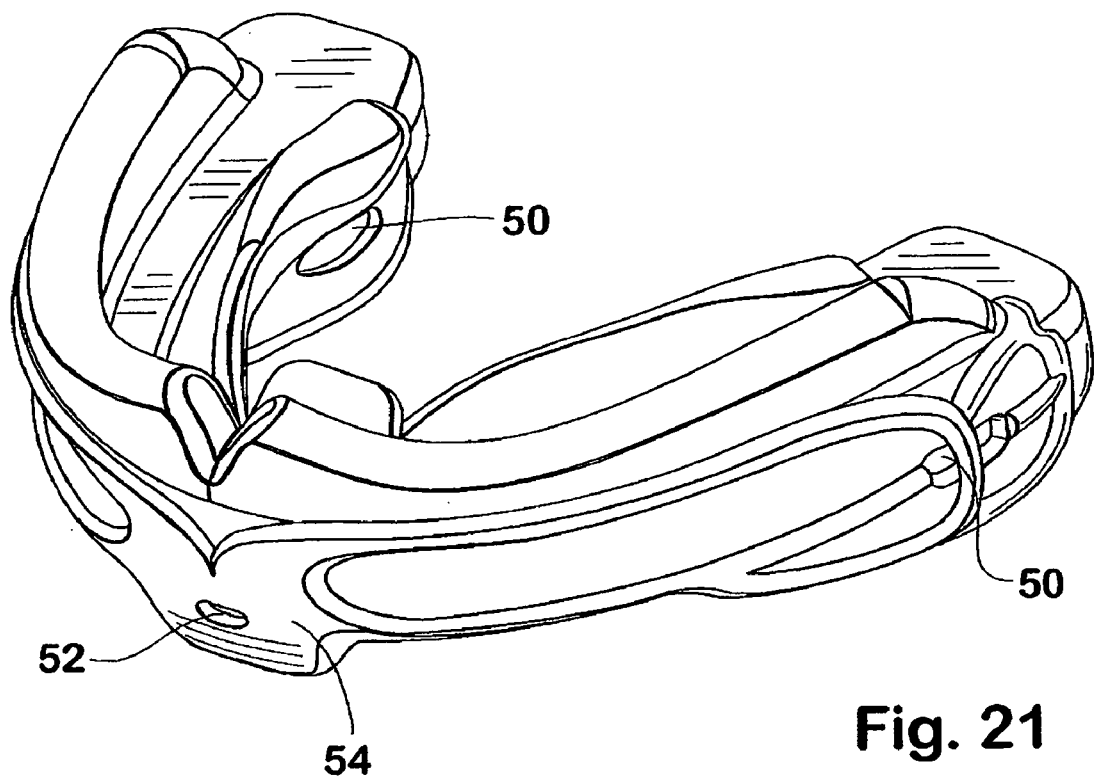
FIG. 21 is a front three dimensional view of the embodiment shown in FIGS. 17-20.

FIGS. 12-21 show embodiments of the present invention that are sportsguards and that contain air spring shock absorbers. Unless otherwise indicated the same reference numerals will be used to indicate the same components.

The sports guard comprises the same structural features as the appliance illustrated in FIGS. 1 to 11. It comprises a base member made of polyethylene that is encapsulated in a layer of EVA material. The EVA material is softened by placing it in hot water and then placed in a user's mouth to shape it to the arch and teeth of a user.

One major difference between this embodiment and the earlier embodiment is that this embodiment only defines an upper channel within which the upper arch of a user is received. The guard would generally be used in contact sports where it acts to resist damage to the teeth and jaw of a user. In particular the guard protects the vulnerable front incisor teeth and the temporomandibular (TMJ) joint of a user. It does not have a lower channel for receiving the lower teeth.

Another difference is that these appliances are equipped with 'air spring' shock absorbers, for absorbing impact shock.

These embodiments are provided with spacings 50, arranged in the rear flanges of the base member and a front spacing 52, arranged at the front of the appliance below the front, upper notch. These spacings 50 provide compressible areas able to absorb impact shock.

FIGS. 17 to 21 illustrate an embodiment that has the air springs described above and also has an additional feature of a brace that is mounted over the layer of EVA extending across the outer flange. Typically the brace is formed in a third moulding process as a layer of thermoplastic rubber superimposed on the layer of EVA. It thus substantially takes on the shape and form of the outer surface of the guard. The brace does however project downwardly below the lower edge of the outer flange as shown in the drawings. Further it should be noted that the brace is only used on an upper arch appliance where there is no channel for the lower teeth.

The function of the brace is primarily to protect the lower teeth. It does this by virtue of the fact that it depends down and thereby covers over the lower teeth when fitted. The brace also assists with the correct positioning of the lower jaw both during use and the initial moulding of the guard. More specifically the rear part of the brace locates and centralizes the lower jaw laterally. The front part of the brace provides a locating formation form correctly positioning the front teeth and the lower jaw by encouraging positioning of the front teeth immediately behind a leading or forwardmost portion of the brace. During initial fitting of the guard the user bites on the heated EVA and the brace optimizes the lower jaw position for the MORA effect.

The rear part of the brace gives added protection from side blows by holding the lower jaw braced from lateral movement. This provides similar features to a double mouthguard but with less bulk and much more freedom of movement whilst still maintaining optimum breathing, speaking and lower front tooth and jaw protection.

Figure 22:
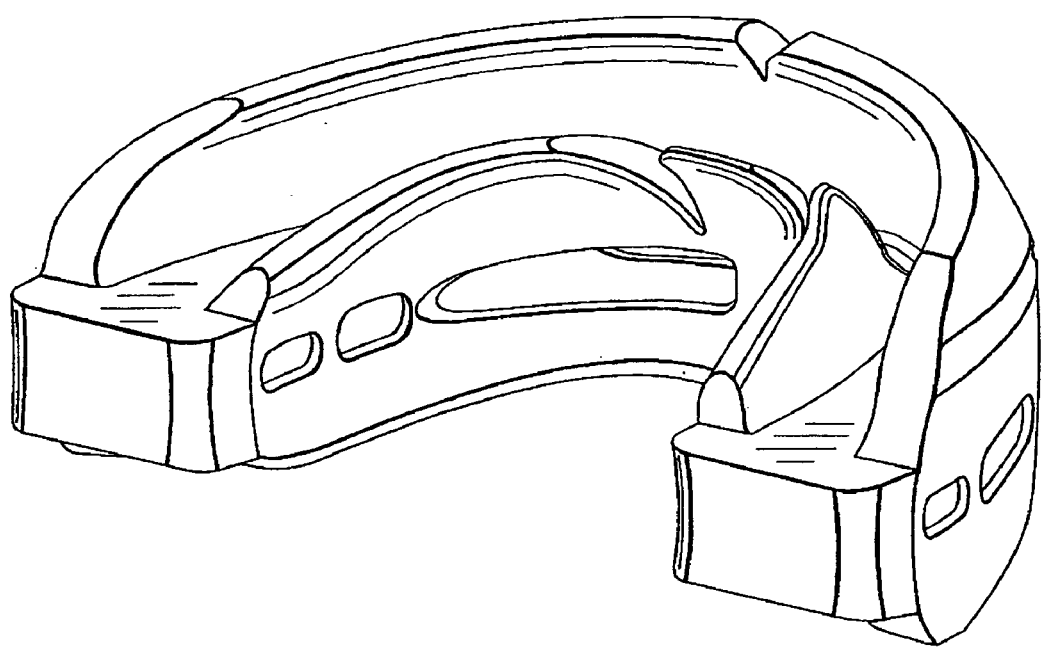
FIG. 22 is a rear three dimensional view of a preferred embodiment of a guard having upper and lower teeth engaging elements.
Figure 23:
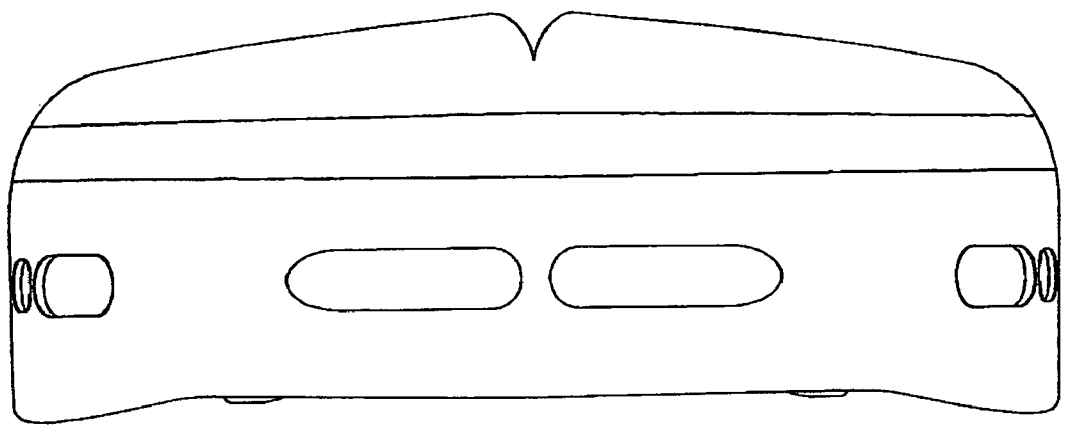
FIG. 23 is a front view of the guard of FIG. 22.
Figure 24:
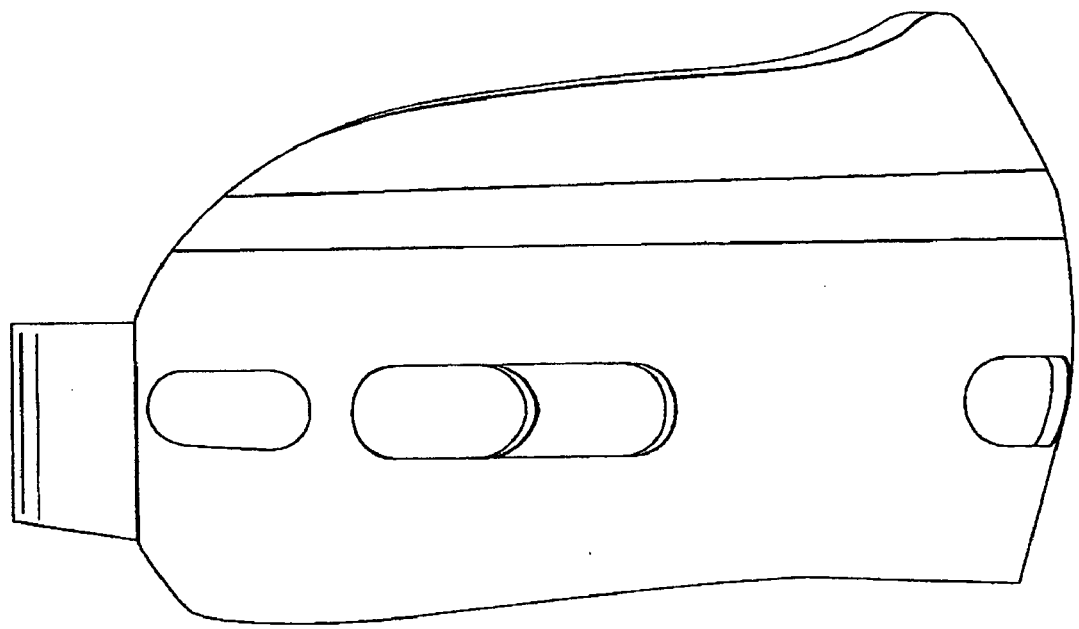
FIG. 24 is a side view of the guard of FIG. 22 and FIG. 23.
Figure 25:
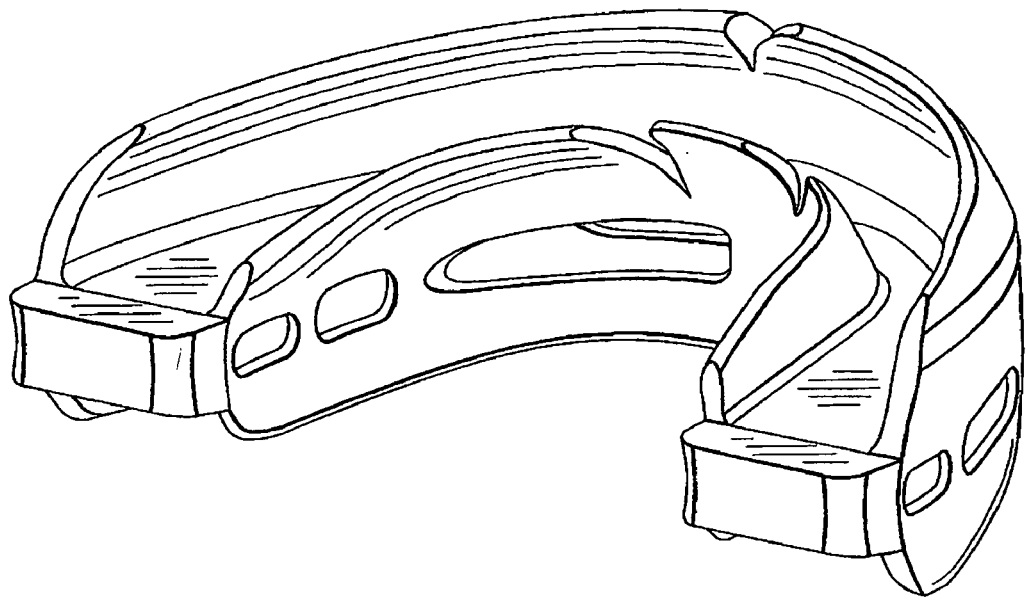
FIG. 25 is a rear three dimensional view of a double mouthguard in accordance with another embodiment.

FIGS. 22-25 show preferred embodiments of a double mouth guard according to the present invention whereby the air springs extend through both the base member and the teeth engaging elements, and decrease in length from the front of the mouth guard to the rear of the mouth guard.

Figure 26:
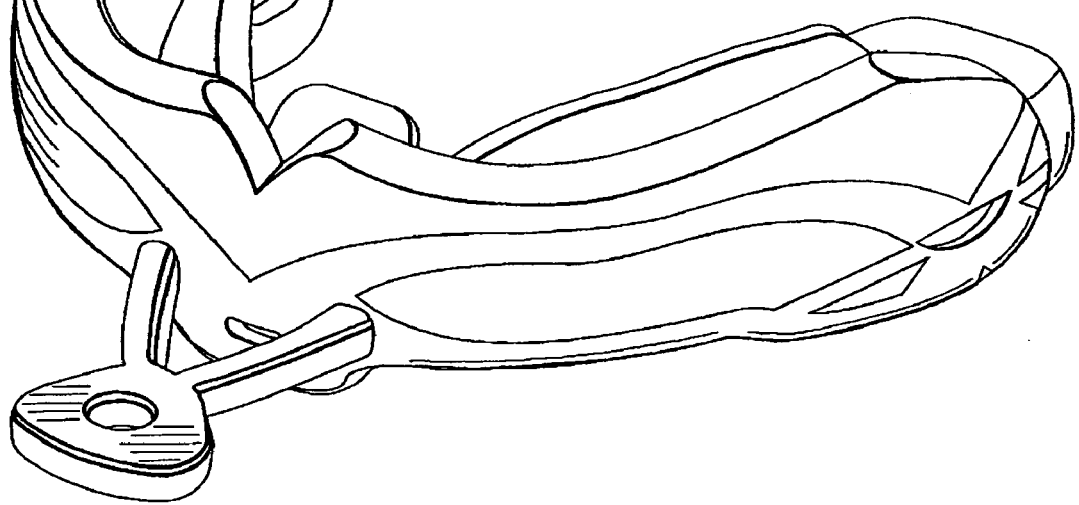
FIG. 26 is a front three dimensional view of a guard in accordance with another embodiment of the invention illustrating an extension attached to a brace, to which extension a cord is attachable for affixing the mouthguard to a face guard or a sports helmet.
Figure 27:
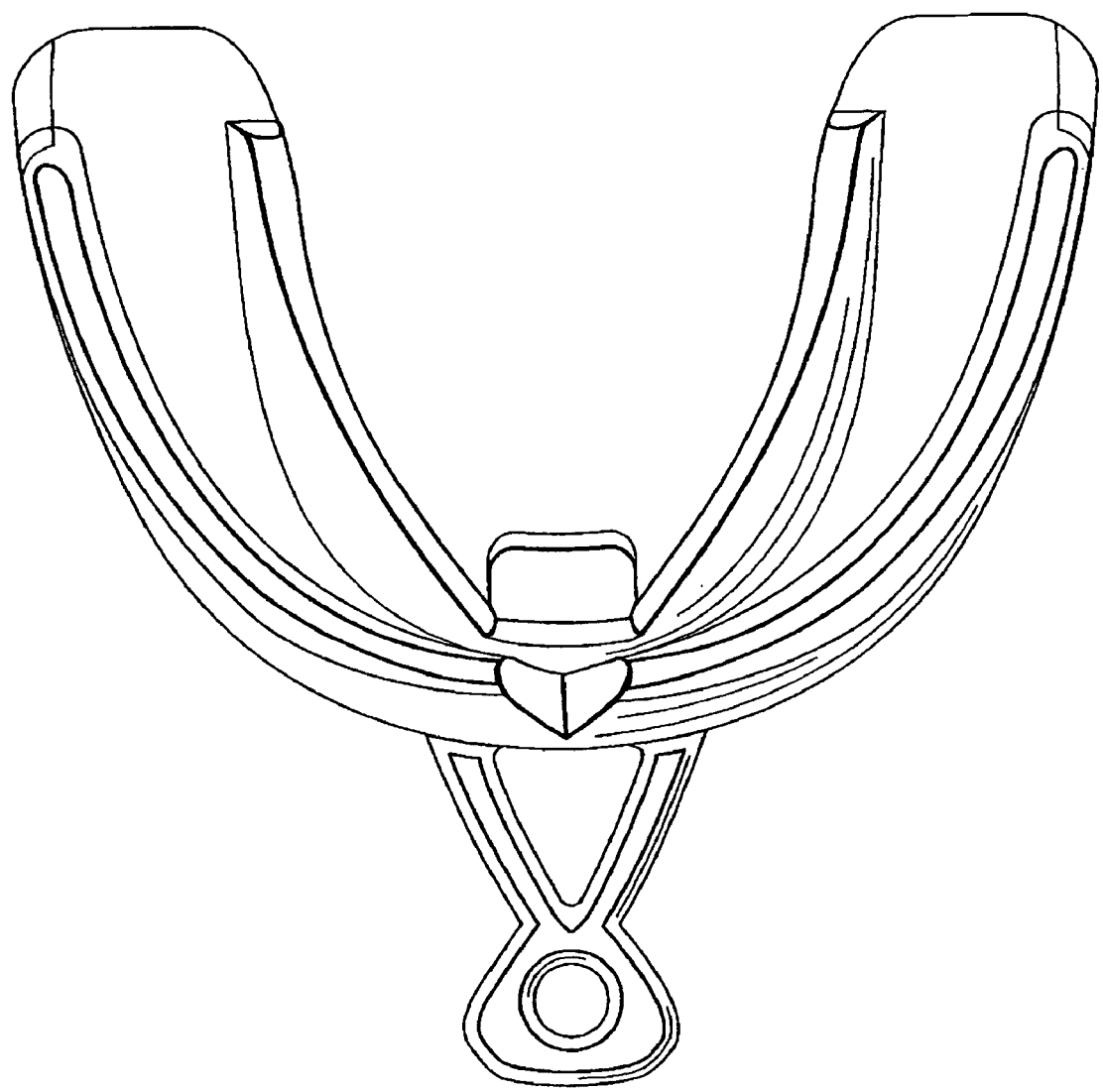
FIG. 27 is a top plan view of the embodiment from FIG. 26.
Figure 28:
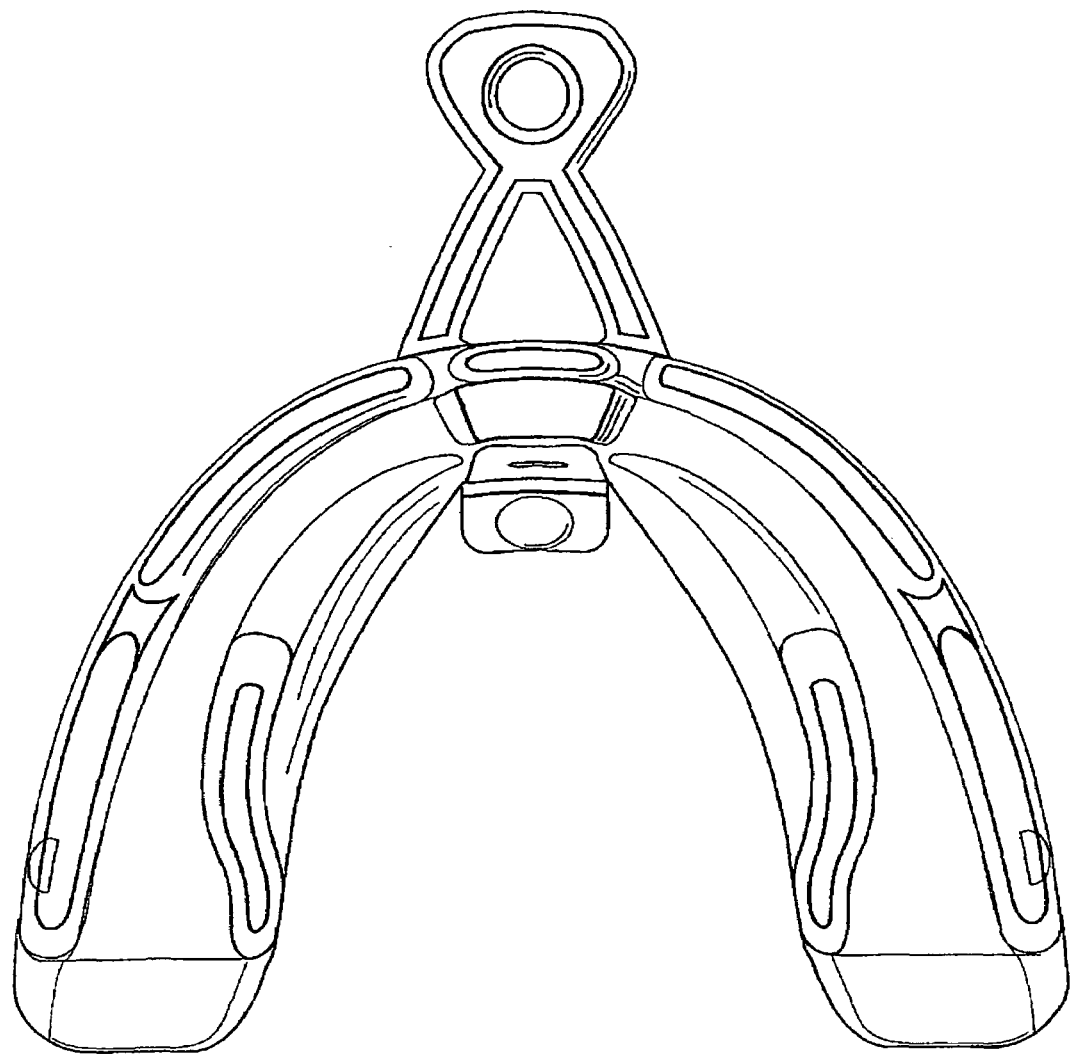
FIG. 28 is a bottom plan view of the embodiment from FIG. 26 and FIG. 27.
Figure 29:
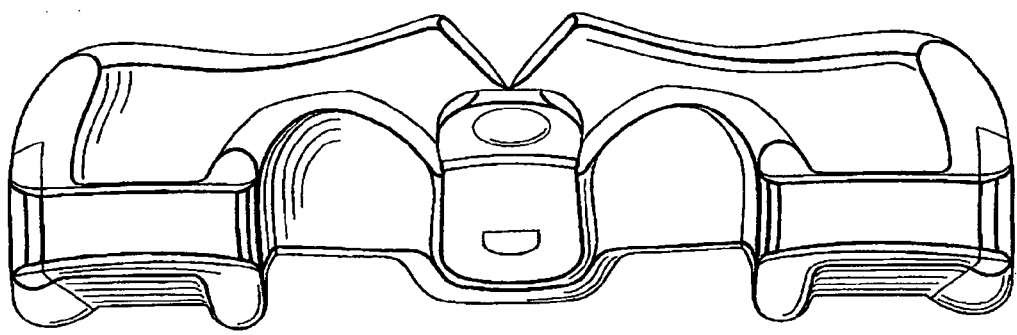
FIG. 29 is a rear view of the embodiment shown in FIGS. 26-28.
Figure 30:
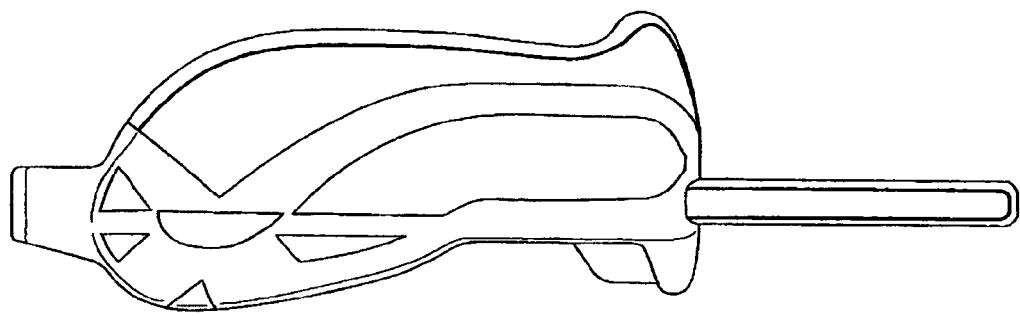
FIG. 30 is a side view of the embodiment shown in FIGS. 26-29.
Figure 31:
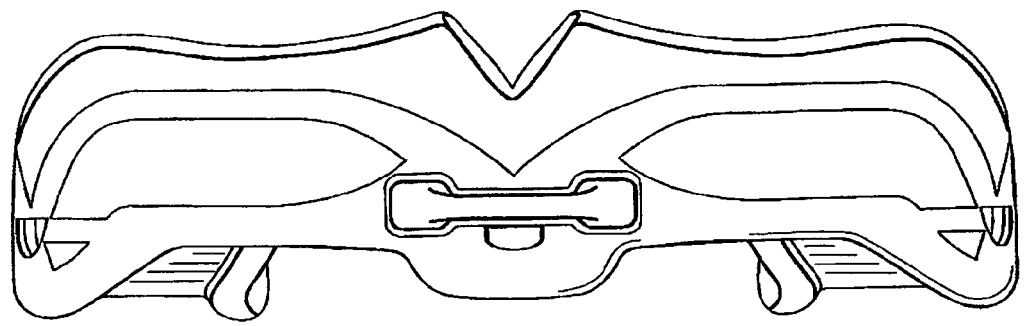
FIG. 31 is a front view of the embodiment shown in FIGS. 26-30.
Figure 32:
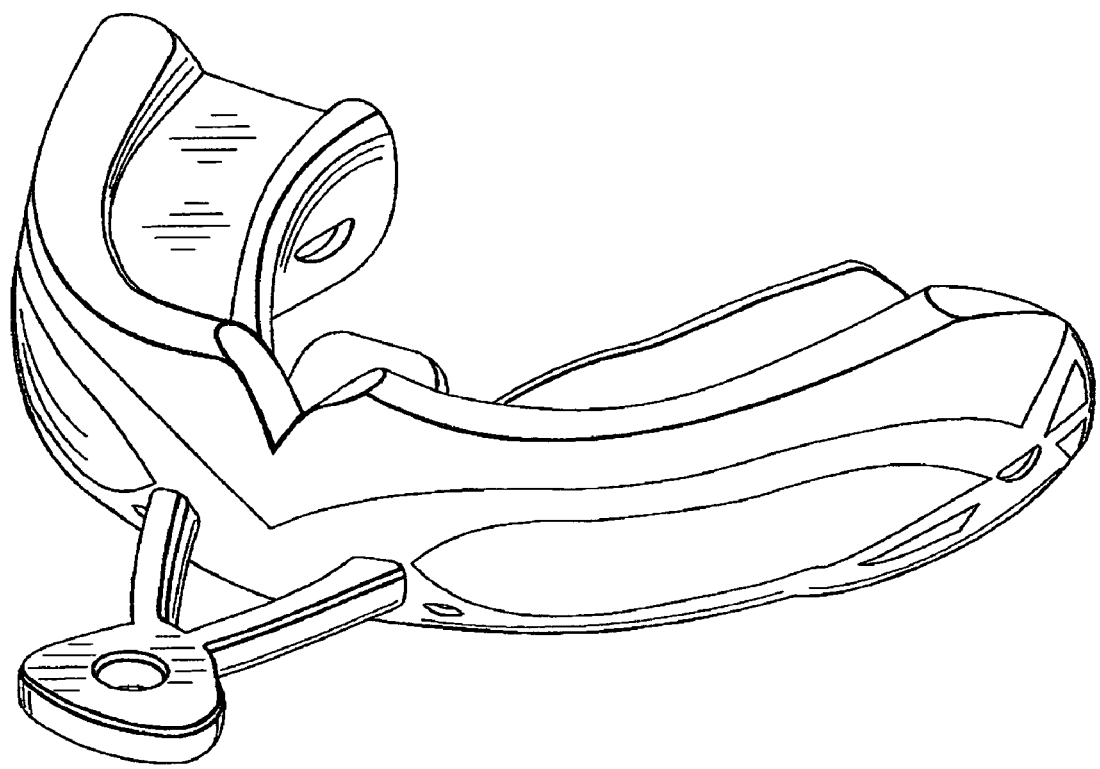
FIGS. 32-37 show a further embodiment of the mouthguard according to the present invention.
Figure 33:
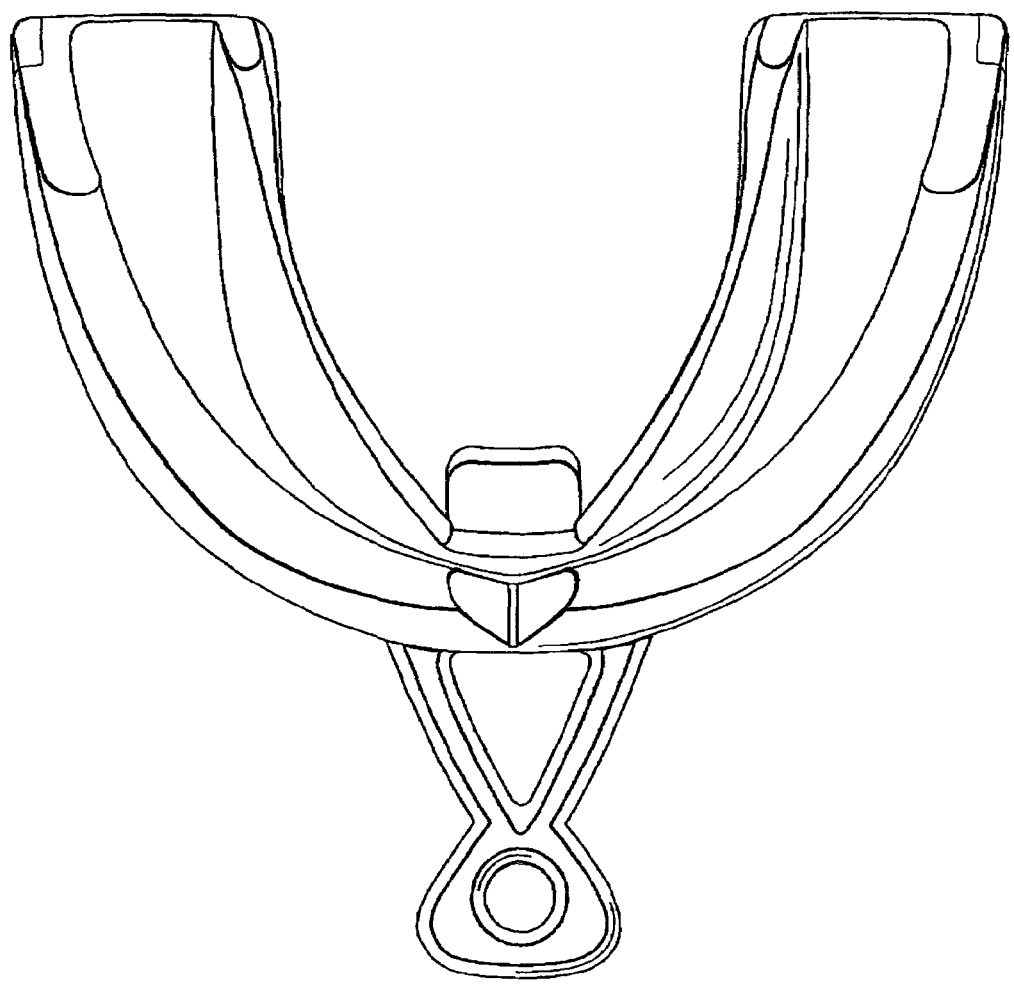
Figure 34:
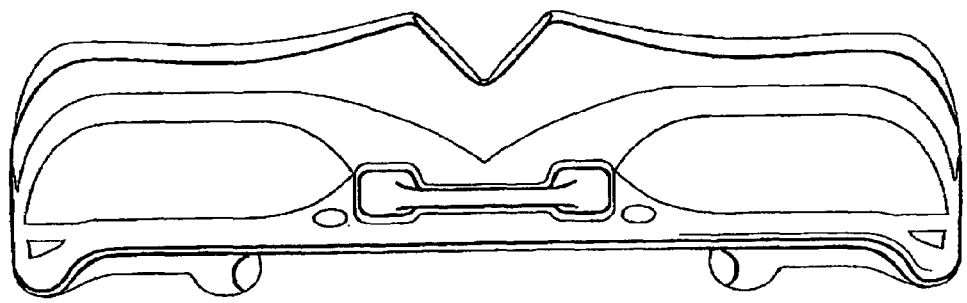
Figure 35:
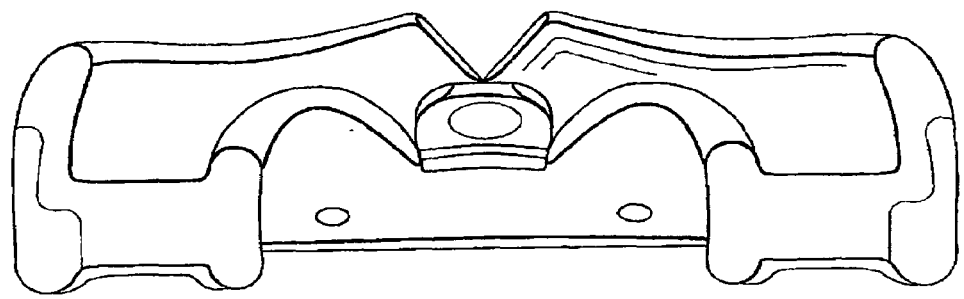
Figure 36:
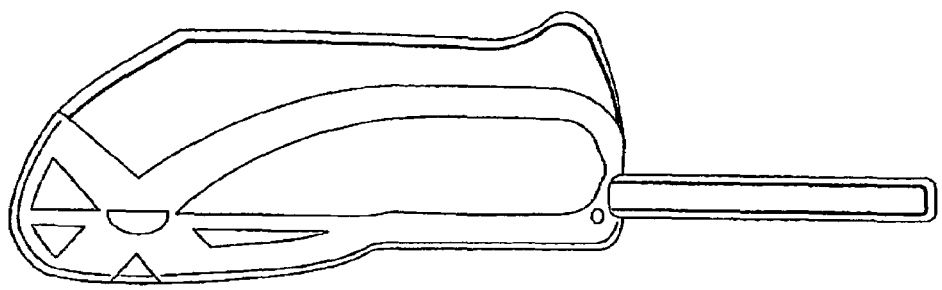
Figure 37:
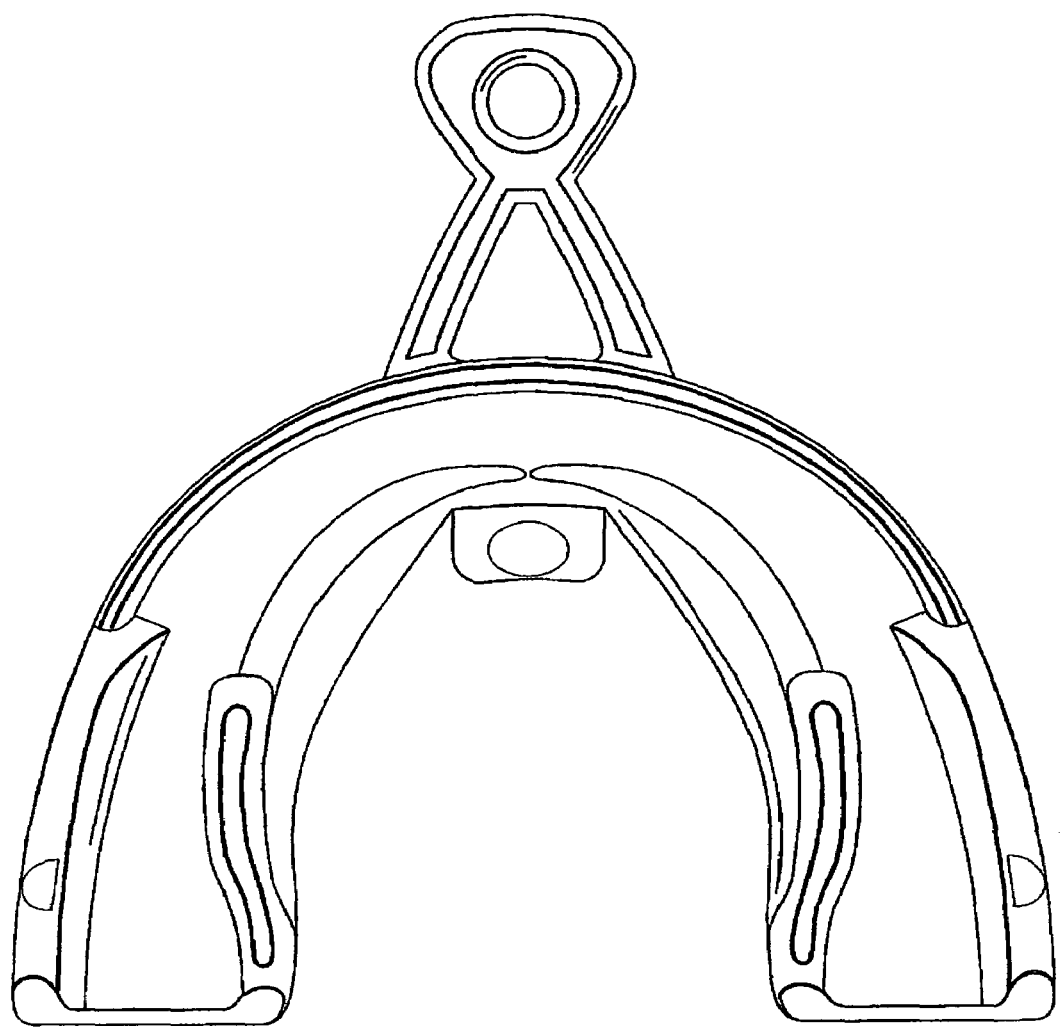
Figure 38:
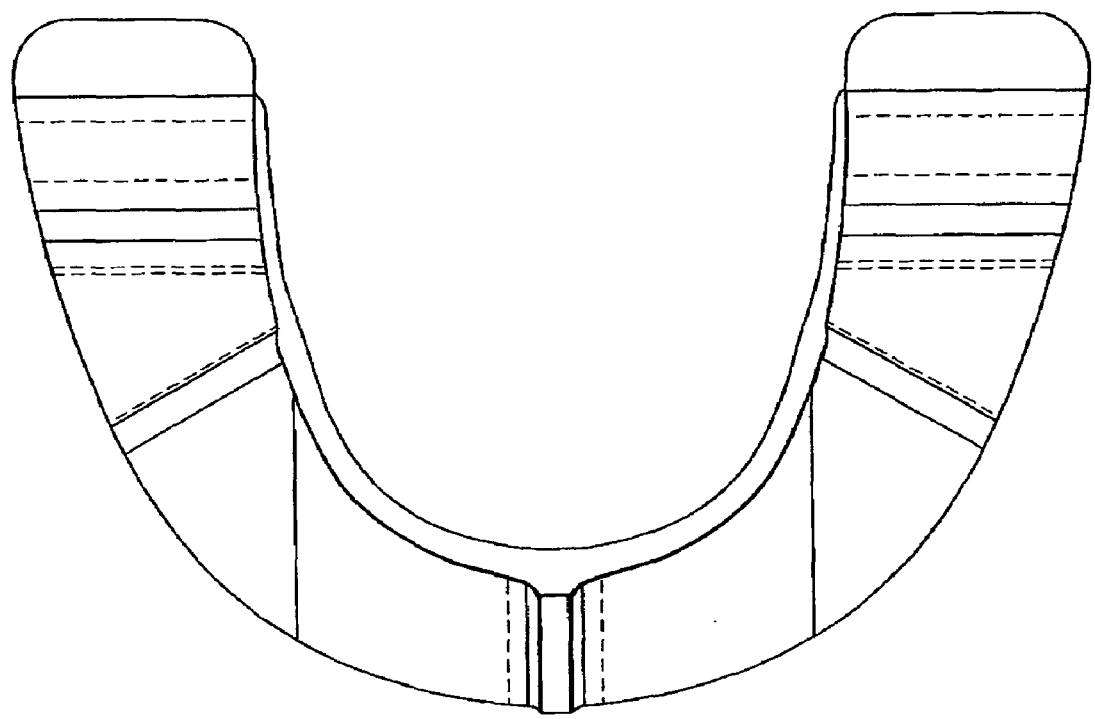
FIG. 38 shows a top plan view of another embodiment.

The embodiments shown in FIGS. 26 to 36 have a handle 60 projecting forwardly from a central region of the outer flange. This handle is used to put the guard inside the mouth and then remove it as required. This occurs in some sports such as gridiron where short spells of intense physical contact are interspersed by spells of inaction when it would be more comfortable for a user to remove the guard from their mouth. The shape of the handle can take many different forms and it is not required to have high strength. It should just be of a size and shape that enables it to be handled easily by a user.

The guards equipped with the 'spring air' shock absorbers have base members with some degree of flexibility. This is conferred by including a component other than polyethylene in the plastics material from which the base member is made as described above with reference to FIGS. 1 to 5. More specifically the plastics material may include an amount of thermoplastics material such as EVA. Generally the plastics material would not contain more than 10% of EVA by weight and more typically about 4-8% by weight. Applicant has found that the addition of this EVA increases the flexibility of the base member somewhat which is advantageous in an impact. At the same time the base member is still sufficiently rigid to hold its shape and also that of the guard overall.

An advantage of the sports guard described above is that when the guard is heated in water it does not change or lose its basic shape. This is because the base member is sufficiently strong and rigid to resist this. The hard base member forces the layer of thermoplastic material against the teeth where it conforms to the contours of the teeth. These guards which are essentially mass produced and are one size fits all produces an excellent fit that is comparable to that achieved with custom made guards produced by taking impressions of a user's mouth and jaw.

A further advantage of the guard described in this application is that it can be remoulded to maintain optimum fit should the fit become loose for any reason. The guard is simply heated again in boiling water and then returned to the mouth of the user where it is reshaped to restore optimum fit. Prior art custom made sports guards of which the applicant is aware are not able to do this.

A further advantage of the guard described above is that it has the ability to spread the force from a blow or impact to the front of the guard across the full body of the guard. It does this because the base member is sufficiently rigid not to deform locally when such an impact occurs. Rather the entire guard absorbs the impact and tends to move in response thereto. By spreading the force over the entire mouth of a user rather than the fragile front teeth, the risk of injury to the front teeth is considerably reduced. The rear molars have a number of extensive roots and are thicker and more robust than the front teeth. They are therefore better adapted to withstand a strong blow to the mouth. Many prior art sports guards do not have this ability. They tend to bend or deform locally in response to a frontal impact, transferring the force of the blow directly to the front teeth.

A further advantage of the guard described above is that the web has an aerofoil shape on each side of the arch extending from the front towards the rear of the arch. Both the base member has an aerofoil shape beneath the thermoplastic layer and the thermoplastic layer also has this shape. The aerofoil fills in the space between the upper and lower teeth and provides support to the TMJ joint. Applicant believes that this feature assists in transferring the shock of a blow to the front of the jaw to all the teeth and from the teeth through to the skull, rather than concentrating the impact at the TMJ which can damage this joint. The rigid base member that cannot easily be deformed provides an appropriate level of support to the TMJ joint.

A yet further advantage of the guard described above is that it has the ability to absorb some of the energy of an impact. It does this by means of the air spring arrangement. The energy which is dissipated is thus not transferred through to the skull of the user and the user is less likely to suffer pain and/or injury.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. An oral appliance for placing in a mouth of a user, the appliance including:
   a base member having a generally U-shaped form corresponding the outline of a jaw of a user, the base member defining at least one channel within which an upper or lower row of teeth of a user can be received, and wherein the base member is made of polyethylene with less than 10% by weight of a thermoplastics material
   a teeth engaging element mounted over the base member in each channel made of a thermoplastics material that is able to be user conformed or user moulded to suit the individual mouth of the user.

2. An oral appliance according to claim 1, wherein the base member is made of polyethylene with 3-8% by weight of thermoplastics material.

3. An oral appliance according to claim 1, wherein the base member is made of polyethylene with 4-6% by weight of thermoplastics material.

4. An oral appliance according to claim 1, wherein the base member is made of high density polyethylene with 4-6% by weight of thermoplastics material which is EVA and each teeth engaging element is made of EVA.

5. An oral appliance according to claim 1, wherein the base member defines only an upper channel within which upper teeth of a user are received.

6. A method according to claim 5 wherein the base member is injection molded from polyethylene, polyurethane, polyethylene, polypropylene or santoprine.

7. A method of manufacturing an oral appliance for placing in the mouth of a user, the method including the steps of:
   molding a base member from plastic material in a first molding step in a first mould, the member having a generally U-shaped form corresponding to the outline of the jaw of a user and inner and outer flanges interconnected by a web which define at least one of upper and lower channels within which the corresponding rows of teeth of a user are received;
   arranging one or more spacings in the base member and;
   removing the base member from the first mould and placing it in a second mould having a larger mould cavity and moulding a continuous layer of thermoplastic material onto the base member to form at least one of the upper and lower teeth engaging elements capable of being customised to suit the mouth of a user, the layer encasing the member to thereby firmly and securely mount the layer of thermoplastic material on the base member.

8. A method according to claim 7 wherein the continuous layer of thermoplastic material is molded substantially fully across the surface area of the base member in said second molding step.

9. A method according to claim 8 wherein the layer of thermoplastic material is injection molded from EVA while it is locked in position in the second mould.

10. Base member for an oral appliance for placing in a mouth of a user, having a generally U-shaped form corresponding to the outline of a jaw of a user, the base member defining at least one channel within which an upper or lower row of teeth of a user can be received, the base member further comprising shock absorbing means taking the form of pre-designated compressible sections in order to substantially absorb impact shock, and further comprising a first material, preferably being polyethylene and a second material, being EVA, wherein the weight percentage of EVA in the base member preferably lies in the range 0.5-10% and is more preferably in the range 4-8%.

11. An oral appliance for placing in mouth of a user, the appliance comprising:
   a base member having a generally U-shaped form corresponding to the outline of a jaw of the user, the base member having an outer surface and an inner surface, said base member defining at least one channel having a surface extending generally transverse to said outer and inner surfaces, said channel being arranged to receive an upper or lower row of teeth of the user, wherein the base member is formed from a rigid plastics material, which is not user conformable or mouldable in boiling water, the rigid plastics material comprises a non-thermoplastic material either alone or in combination with another plastics material, and the non-thermoplastic material comprises polyethylene on its own;
   a tongue tag on the inner flange of the base member, the tongue tag being substantially centrally positioned for correctly positioning the tongue of a user during use, and a cut out defined in the outer flange of the base member for allowing the appliance to adapt to varying arch sizes, and breathing apertures defined in the base member for facilitating breathing by a user when wearing the appliance;
   a teeth engaging element, mounted on the surface of said at least one channel, comprising a layer of a material able to be user conformed to suit the individual mouth of the user; and
   shock absorption means associated with the base member and/or teeth engaging element for absorbing impact shock, said shock absorption means comprising at least one air channel defined in the base member and extending from said outer surface to said inner surface.

12. Oral appliance according to claim 11 further including locating means for correctly locating and position the jaws in the teeth engaging element during fitting of the oral appliance wherein the locating means comprises a brace arranged externally on the teeth engaging element.

13. Oral appliance according to claim 12 wherein the brace comprises rubber.

* * * * *